(12) United States Patent
Shangguan et al.

(10) Patent No.: US 12,365,903 B2
(45) Date of Patent: Jul. 22, 2025

(54) APPLICATION OF APTAMER IN RECOGNITION AND BINDING OF ALKALINE PHOSPHATASE HETERODIMER OR TUMOR DETECTION

(71) Applicant: INSTITUTE OF CHEMISTRY, CHINESE ACADEMY OF SCIENCES, Beijing (CN)

(72) Inventors: Dihua Shangguan, Beijing (CN); Tao Bing, Beijing (CN); Luyao Shen, Beijing (CN); Xiangjun Liu, Beijing (CN); Nan Zhang, Beijing (CN); Junyan Wang, Beijing (CN)

(73) Assignee: INSTITUTE OF CHEMISTRY, CHINESE ACADEMY OF SCIENCES, Beijing (CN)

( * ) Notice: Subject to any disclaimer, the term of this patent is extended or adjusted under 35 U.S.C. 154(b) by 1242 days.

(21) Appl. No.: 16/967,102

(22) PCT Filed: Jan. 23, 2019

(86) PCT No.: PCT/CN2019/072749
§ 371 (c)(1),
(2) Date: Aug. 3, 2020

(87) PCT Pub. No.: WO2019/149115
PCT Pub. Date: Aug. 8, 2019

(65) Prior Publication Data
US 2020/0362349 A1    Nov. 19, 2020

(30) Foreign Application Priority Data

Feb. 2, 2018   (CN) .......................... 201810105373.3
Jan. 2, 2019   (CN) .......................... 201910001280.0

(51) Int. Cl.
*C12N 15/115*   (2010.01)
*G01N 33/53*    (2006.01)
*G01N 33/574*   (2006.01)

(52) U.S. Cl.
CPC ....... *C12N 15/115* (2013.01); *G01N 33/5308* (2013.01); *G01N 33/57411* (2013.01); *G01N 33/57415* (2013.01); *G01N 33/57419* (2013.01); *G01N 33/57438* (2013.01); *C12N 2310/16* (2013.01); *G01N 2333/916* (2013.01)

(58) Field of Classification Search
None
See application file for complete search history.

(56) References Cited

U.S. PATENT DOCUMENTS

2008/0003563 A1   1/2008   Klock et al.

FOREIGN PATENT DOCUMENTS

| CN | 102352311 A | 2/2012 |
|----|-------------|--------|
| CN | 105624166 A | 6/2016 |
| CN | 106841613 A | 6/2017 |
| CN | 115058429   | * 9/2022 |

OTHER PUBLICATIONS

Dua et al., "Alkaline Phosphatase ALPPL-2 Is a Novel Pancreatic Carcinoma-Associated Protein". Cancer Res. Mar. 14, 2013. 73(6): 1934-1945 (Year: 2013).*
Torzewski et al. Hindawl Publishing Corporation, Mediators of Inflammation, vol. 2014, pp. 1-7 (Year: 2014).*
Van Der Veklens et al. Cardiovascular Endocrinology vol. 2, pp. 67-76 (Year: 2013).*
Dua et al, "Alkaline Phosphatase ALPPL-2 Is a Novel Pancreatic Carcinoma-Associated Protein", Cancer Research, 73(6) Mar. 15, 2013, pp. 1934-1945.
Peng et al. "Application of Aptamers Conjugated Inorganic Nanomaterial in Tumor Research", Biotechnology Bulletin, 2017, 33(11), pp. 48-53.
Wang et al., "Research on Clinical Significance of Alkaline Phosphatase on Tumor Diagnosis", Journal of Clinical Psychosomatic Diseases, vol. 22, May 31, 2016 (May 31, 2016), pp. 47-48.
Sun et al., "Simple Analysis on Clinical Significance of Examination of Alkaline Phosphatase and Isoenzyme thereof", Diet Health, vol. 4, No. (16), Aug. 31, 2017 (Aug. 31, 2017), p. 12.
Wang et al., "Amplified Graphene Oxide-based Assay of Alkaline Phosphatase", Shandong Chemical Industry, vol. 46, No. (9), Dec. 31, 2017 (Dec. 31, 2017), pp. 63-65.
International search report dated Apr. 24, 2019 from corresponding application No. PCT/CN2019/072749.

* cited by examiner

*Primary Examiner* — Brian Whiteman
(74) *Attorney, Agent, or Firm* — HAUPTMAN HAM, LLP

(57) ABSTRACT

The present invention discloses the application of aptamer in recognition and binding of alkaline phosphatase heterodimer. The present invention provides an aptamer or its derivative, the nucleotide sequence of which is shown in SEQ ID NO: 1 in the sequence listing. The present invention also provides a kit including an aptamer or a derivative thereof, and a carrier for fixing or coupling the aptamer or a derivative thereof, wherein the aptamer is a single-stranded DNA molecule having the nucleotide sequence as shown in SEQ ID NO: 1. The method for capturing and detecting circulating tumor cells, exosomes and free alkaline phosphatase in peripheral blood highly expressing alkaline phosphatase based on the aptamer magnetic nanoparticle technology of the present invention can achieve highly selective capture and detection of target cells, exosomes or free proteins.

9 Claims, 4 Drawing Sheets
Specification includes a Sequence Listing.

APPLICATION OF APTAMER IN RECOGNITION AND BINDING OF ALKALINE PHOSPHATASE HETERODIMER OR TUMOR DETECTION

RELATED APPLICATIONS

The present application is a National Phase of International Application Number PCT/CN2019/072749, filed Jan. 23, 2019, and claims the priority of China Application No. 201910001280.0, filed Jan. 2, 2019; and claims the priority of China Application No. 201810105373.3, filed Feb. 2, 2018.

INCORPORATION BY REFERENCE

The sequence listing provided in the file entitled Sequence_Listing_20241105.docx, which is an ASCII text file that was created on Nov. 5, 2024, and which comprises 4,969 bytes, is hereby incorporated by reference in its entirety.

TECHNICAL FIELD

The present invention belongs to the technical field of biotechnology and clinical medicine, and particularly relates to applications of aptamers in recognition and binding of alkaline phosphatase heterodimer or tumor detection.

BACKGROUND ART

An aptamer is a type of single-stranded DNA, RNA, peptide nucleic acid or chemically modified nucleic acid sequence that can specifically interact with a target substance, usually consisting of 15-80 nucleotides. Aptamers can form specific three-dimensional structures to bind with high affinity to target molecules, such as hairpins, pseudo knots, G-quadruplexes, etc. The highly specific binding is achieved by intermolecular interactions, such as van der Waals force, hydrogen bonding, electrostatic interaction and hydrophobic interaction. Aptamers are called "chemical antibodies" because of their high affinity, good specificity, no immunogenicity, easy synthesis and modification, good biochemical stability, reversibility and renaturation, etc.

Aptamers can be used in the fields of diagnosis and detection of some diseases, drug target localization, new drug development and delivery-related drug molecules, etc. At present, aptamers for the treatment of cancer, AIDS and other diseases are also emerging. For example, the VEGF-targeted aptamer (pegaptanib sodium, trade name: MACUGEN®) developed by Eyetch/Pfizer has been approved by the FDA in 2004 and is successfully used to treat age-related macular degeneration. In recent years, the method of using cell-SELEX technology to screen specific aptamers and then find tumor markers has good application prospects. However, there are only very few successful cases. The bottleneck problem lies in the purification/identification of target molecules of aptamer located on the cell membrane.

Alkaline phosphatase (ALP or AKP) is an enzyme widely distributed in the liver, bone, intestine, kidney and placenta of the human body and excreted from the liver to the gallbladder, can directly participate in phosphorus metabolism, and play an important role in the digestion, absorption, secretion and ossification processes of calcium and phosphorus. This enzyme can catalyze the removal of 5' phosphate groups from nucleic acid molecules, thereby converting the 5'-P ends of DNA or RNA fragments into 5'-OH ends. But it is not a single enzyme, it is a group of isozymes. Currently known human isozymes include: tissue non-specific alkaline phosphatase (TNAP), intestinal alkaline phosphatase (IAP), placental alkaline phosphatase (PALP) and placental-like alkaline phosphatase (GCAP). The alkaline phosphatase in the serum of normal people mainly comes from liver and bone. The determination of alkaline phosphatase is mainly used to diagnose hepatobiliary and skeletal system diseases, which is an important indicator reflecting extrahepatic biliary tract obstruction, intrahepatic space-occupying lesions and rickets.

Alkaline phosphatase heterodimer is overexpressed in colorectal cancer, breast cancer, hepatocellular carcinoma, cervical cancer and other tumor tissues. Free alkaline phosphatase heterodimers, exosomes or circulating tumor cells containing alkaline phosphatase heterodimers can be released into the bloodstream from the primary tumor or metastatic lesion. Therefore, the detection of free alkaline phosphatase heterodimers, exosomes or circulating tumor cells will contribute to early diagnosis and screening of tumors, monitoring of the recurrence and metastasis of postoperative tumors, evaluation of the sensitivity of antitumor drugs, patient prognosis and selection of individualized treatment strategies.

Circulating tumor cells refer to tumor cells that spread and survive in peripheral blood during the development of malignant tumors and are closely related to tumor metastasis and prognosis. The detection of circulating tumor cells refers to the method of analyzing circulating tumor cells in the peripheral blood of tumor patients. The detection of circulating tumor cells in peripheral blood is the most direct and important method for predicting tumor metastasis, which is of great significance in clinical diagnosis, prognostic judgment and efficacy monitoring of early tumor metastasis. The discovery of circulating tumor cells is expected to change the current clinical situation that still depends on imageological examinations and traditional tumor markers. Because the circulating tumor cells in peripheral blood are extremely rare, there are extremely high requirements on the sensitivity and selectivity of the detection technology. At present, there are many methods for the detection of circulating tumor cells. First, the circulating tumor cells are separated and enriched by methods such as density gradient centrifugation, cell filtration or adhesion technology, immunomagnetic beads separation technique and microfluidic chip technology, and then detected by immunocytochemistry, reverse transcription polymerase chain reaction and flow cytometry. At present, the only method approved by the US Food and Drug Administration (FDA) to detect circulating tumor cells is the CELLSEARCH® system. Although this system can achieve the capture and detection of circulating tumor cells, its sensitivity and specificity still need to be further improved, and it should be fast, simple and high throughput.

Exosome is a nano-scale lipid inclusion structure with a diameter of 30-100 nm, which is encapsulated with proteins, mRNA and microRNA, etc. Almost all types of cells, including tumor cells, can produce and release exosomes. Exosomes are released by cell secretion, spread in blood and other body fluids, and finally can be engulfed by other cells, which is an important medium for intercellular communication. More and more studies have found that exosomes secreted by host cells or tumor cells are involved in tumorigenesis, growth, invasion and metastasis, so the detection and research of exosomes have received more and more attention.

SUMMARY OF THE INVENTION

One object of the present invention is to provide an aptamer or its derivatives.

The aptamer or its derivative provided by the present invention is any one of the following 1)-7):
1) a single-stranded DNA molecule having the nucleotide sequence as shown in SEQ ID NO: 1;
2) a derivative of an aptamer obtained by deletion or addition of one or more nucleotides in the aptamer defined in 1) and having the same function as the aptamer;
3) a derivative of an aptamer obtained by nucleotide substitution or modification in the aptamer defined in 1) and having the same function as the aptamer;
4) a derivative of an aptamer obtained by modifying the backbone of the aptamer defined in 1) (i.e., the stem formed by the nucleotides in positions 1-7 and 37-44 of SEQ ID NO: 1) into a thiophosphate backbone and having the same function as the aptamer;
5) an RNA molecule encoded by the aptamer defined in 1) and having the same function as the aptamer;
6) a peptide nucleic acid molecule encoded by the aptamer defined in 1) and having the same function as the aptamer;
7) a derivative of an aptamer obtained by attaching a signal molecule and/or an active molecule and/or a functional group and/or a radionuclide to one end or the middle of the aptamer defined in any one of 1) to 6) and having the same function as the aptamer.

In the above aptamer or its derivative, the derivative of the aptamer is obtained by removal or alteration of the nucleotides in positions 1-7 from the first nucleotide at the 5' end (including the first nucleotide residue at the 5' end) of the nucleotide sequence of the aptamer as shown in SEQ ID NO: 1; and/or, the derivative of the aptamer is obtained by removal of the nucleotides in positions 1-7 from the first nucleotide at the 3' end (including the first nucleotide residue at the 3' end) of the nucleotide sequence of the aptamer as shown in SEQ ID NO: 1; or, the derivative of the aptamer is composed of the retained nucleotide residues after addition of several nucleotides or modifying groups to the 5' end or 3' end of the nucleotide sequence of the aptamer as shown in SEQ ID NO: 1 without affecting the structure (G-quadruplex structure) formed by the nucleotides in positions 10-36 of SEQ ID NO: 1.

In the above aptamer or its derivative, the derivative of the aptamer is any one of the following 1) to 6):
1) a single-stranded DNA molecule having the nucleotide sequence as shown in SEQ ID NO: 2;
2) a single-stranded DNA molecule having the nucleotide sequence as shown in SEQ ID NO: 3;
3) a single-stranded DNA molecule having the nucleotide sequence as shown in SEQ ID NO: 4;
4) a single-stranded DNA molecule having the nucleotide sequence as shown in SEQ ID NO: 5;
5) a single-stranded DNA molecule having the nucleotide sequence as shown in SEQ ID NO: 6;
6) a single-stranded DNA molecule having the nucleotide sequence as shown in SEQ ID NO: 7.

In the above aptamer or its derivative, the derivative of the aptamer is obtained by labeling a fluorescent group, a biotin group or a radionuclide at the 5' end or 3' end of the aptamer defined in any one of 1)-6).

Use of the aptamer or its derivative in at least one of the following 1)-4) is also within the protection scope of the present invention:
1) detection or diagnosis of alkaline phosphatase;
2) preparation of products for detection or diagnosis of alkaline phosphatase;
3) extraction or capture of alkaline phosphatase;
4) preparation of products for extraction or capture of alkaline phosphatase;

the target of the detection or diagnosis or extraction or capture is alkaline phosphatase itself, an alkaline phosphatase heterodimer, cells containing alkaline phosphatase or its heterodimer, exosomes containing alkaline phosphatase or its heterodimers, tissue sections containing alkaline phosphatase or its heterodimers, living animals containing alkaline phosphatase or its heterodimers.

In the above use, the sample for the detection or diagnosis is whole blood, serum, culture, saliva, urine, tissue section or living body; or the detection or diagnosis method is fluorescence imaging, such as fluorescence imaging of cells, fluorescence imaging of tissue sections, fluorescence imaging of living bodies, by a microscopic examination.

Use of the aptamer or its derivative in at least one of the following a1-a26 is also within the protection scope of the present invention:
a1) enrichment and extraction of alkaline phosphatase;
a2) recognition and binding of alkaline phosphatase or assistance in recognition and binding of alkaline phosphatase;
a3) recognition and binding of cells expressing alkaline phosphatase or assistance in recognition and binding of cells expressing alkaline phosphatase;
a4) detection of the content or activity of alkaline phosphatase in samples to be tested;
a5) detection of the presence or absence of alkaline phosphatase in samples to be tested;
a6) detection of substances that bind to antibodies against alkaline phosphatase;
a7) detection of proteins that interact with alkaline phosphatase;
a8) preparation of products for enrichment and extraction of alkaline phosphatase;
a9) preparation of products for recognition and binding of alkaline phosphatase or assistance in recognition and binding of alkaline phosphatase;
a10) preparation of products for detection of the content or activity of alkaline phosphatase in samples to be tested;
a11) preparation of products for detection of the presence or absence of alkaline phosphatase in samples to be tested;
a12) preparation of products for detection of substances that bind to antibodies against alkaline phosphatase;
a13) preparation of products for detection of proteins that interact with alkaline phosphatase;
a14) preparation of products for diagnosis and/or treatment of diseases related to alkaline phosphatase;
a15) capture and/or detection of cells or exosomes expressing or overexpressing alkaline phosphatase;
a16) preparation of products for capture and/or detection of cells or exosomes expressing or overexpressing alkaline phosphatase;
a17) preparation of probes for animal imaging targeting alkaline phosphatase;
a18) preparation of products for alkaline phosphatase-targeted therapies;
a19) detection or capture of tumors or tumor cells expressing or overexpressing alkaline phosphatase in samples to be tested;
a20) detection or capture of circulating tumor cells expressing or overexpressing alkaline phosphatase in samples to be tested;

a21) detection or capture of exosomes expressing or overexpressing alkaline phosphatase in samples to be tested;
a22) detection or capture of soluble alkaline phosphatase in samples to be tested;
a23) preparation of products for detection or capture of tumors or tumor cells expressing or overexpressing alkaline phosphatase in samples to be tested;
a24) preparation of products for detection or capture of circulating tumor cells expressing or overexpressing alkaline phosphatase in samples to be tested;
a25) preparation of products for detection or capture of exosomes expressing or overexpressing alkaline phosphatase in samples to be tested;
a26) preparation of products for detection or capture of soluble alkaline phosphatase in samples to be tested.

Another object of the present invention is to provide a kit.

The kit provided by the present invention includes the aptamer or its derivative, and a carrier for fixing or coupling the aptamer or its derivative.

In the above kit, the kit has at least one function of the following b1-b11:
b1) enrichment and extraction of alkaline phosphatase;
b2) recognition and binding of alkaline phosphatase or assistance in recognition and binding of alkaline phosphatase;
b3) recognition and binding of cells expressing alkaline phosphatase or assistance in recognition and binding of cells expressing alkaline phosphatase;
b4) detection of the content or activity of alkaline phosphatase in samples to be tested;
b5) detection of the presence or absence of alkaline phosphatase in samples to be tested;
b6) detection of substances that bind to antibodies against alkaline phosphatase;
b7) detection of proteins that interact with alkaline phosphatase;
b8) detection or capture of tumors or tumor cells expressing or overexpressing alkaline phosphatase in samples to be tested;
b9) detection or capture of circulating tumor cells expressing or overexpressing alkaline phosphatase in samples to be tested;
b10) detection or capture of exosomes expressing or overexpressing alkaline phosphatase in samples to be tested;
b11) detection or capture of soluble alkaline phosphatase in samples to be tested.

In the above kit, the carrier for fixing or coupling the aptamer or its derivative can comprise a nano-sized particle, a micro-sized particle, or a chip. The carrier in an embodiment is a magnetic nanoparticle, which is a superparamagnetic magnetic nanoparticle (200 nm) with streptavidin modification on the surface, not only plays a role of size enlargement, but also can be used for magnetic separation operations to achieve high-efficiency capture. It is not limited to magnetic spheres, but can be substrates, such as chips.

The fixing or coupling the aptamer or its derivative is carried out by coupling. Coupling refers to connecting together by covalent couplings, hydrophobic interactions or intermolecular forces. In an embodiment, the connection realized by the interaction between streptavidin and biotin is involved.

In the above kit, the carrier for fixing or coupling the aptamer or its derivative is a nano-sized particle or a micro-sized particle or a chip.

In the above kit, the nano-sized particle is a nano/micro-sized particle modified by a modifier; or
the nano-sized particle is a magnetic nanoparticle; or
the modifier is streptavidin, biotin, a carboxyl group, an amino group or a thiol group.

The above kit also includes a chromogenic substrate that reacts with alkaline phosphatase; the chromogenic substrate is a fluorescent substrate molecule, a chemiluminescent substrate molecule or a visible light-emitting substrate molecule.

The chromogenic substrate is a fluorescent substrate molecule, a chemiluminescent substrate molecule or a visible light-emitting substrate molecule or other alkaline phosphatase substrates. One embodiment of the present invention relates to p-nitrophenyl phosphate disodium (pNPP), which reacts with alkaline phosphatase to produce p-nitrophenol. p-nitrophenol is yellow under alkaline conditions and the absorbance can be detected at 405 nm. The present invention also involves the reaction of BCIP/NBT with alkaline phosphatase to produce a blue-purple precipitate. The present invention also involves the reaction of fluorescein diphosphate with alkaline phosphatase to produce green fluorescence.

The above kit also includes red blood cell lysis buffer and a magnetic separation rack; if the sample to be tested is whole blood, red blood cell lysis buffer is included, and if the sample to be tested is serum or plasma or saliva, red blood cell lysis buffer is not needed.

The cells expressing or overexpressing alkaline phosphatase are tumor cells expressing or overexpressing alkaline phosphatase; and/or the tumor cells expressing or overexpressing alkaline phosphatase are human cervical cancer cells, human breast cancer cells, human colon cancer cells or human hepatocellular carcinoma cells; and/or the circulating tumor cells expressing or overexpressing alkaline phosphatase are circulating tumor cells of human cervical cancer, circulating tumor cells of human breast cancer, circulating tumor cells of human colon cancer or circulating tumor cells of human hepatocellular carcinoma.

Use of the aptamer or its derivative, and the carrier for fixing or coupling the aptamer or its derivative in the preparation of products having at least one function of the following b1-b11 is also within the protection scope of the present invention:
b1) enrichment and extraction of alkaline phosphatase;
b2) recognition and binding of alkaline phosphatase or assistance in recognition and binding of alkaline phosphatase;
b3) recognition and binding of cells expressing alkaline phosphatase or assistance in recognition and binding of cells expressing alkaline phosphatase;
b4) detection of the content or activity of alkaline phosphatase in samples to be tested;
b5) detection of the presence or absence of alkaline phosphatase in samples to be tested;
b6) detection of substances that bind to antibodies against alkaline phosphatase;
b7) detection of proteins that interact with alkaline phosphatase;
b8) detection or capture of tumors or tumor cells expressing or overexpressing alkaline phosphatase in samples to be tested;
b9) detection or capture of circulating tumor cells expressing or overexpressing alkaline phosphatase in samples to be tested;

b10) detection or capture of exosomes expressing or overexpressing alkaline phosphatase in samples to be tested;

b11) detection or capture of soluble alkaline phosphatase in samples to be tested.

The sample to be tested is peripheral whole blood, peripheral blood serum or peripheral blood plasma, cell culture or saliva.

In an embodiment of the present invention, the sample to be tested corresponding to circulating tumor cells expressing or overexpressing alkaline phosphatase is peripheral whole blood;

the sample to be tested corresponding to exosomes expressing or overexpressing alkaline phosphatase is peripheral blood serum or peripheral blood plasma;

the sample to be tested corresponding to free proteins expressing or overexpressing alkaline phosphatase is peripheral blood serum, peripheral blood plasma or saliva.

The third object of the present invention is to provide a method for capturing and/or detecting whether a sample to be tested contains tumor cells expressing or overexpressing alkaline phosphatase, comprising the following steps:

1) preparing aptamer magnetic nanoparticles and removing red blood cells of the sample to be tested;

the sample to be tested is peripheral whole blood;

the method for preparing aptamer magnetic nanoparticles is connecting magnetic nanoparticles and alkaline phosphatase aptamers to obtain aptamer magnetic nanoparticles;

the method for preparing aptamer magnetic nanoparticles is coupling the streptavidin-modified magnetic nanoparticles and the biotin-labeled alkaline phosphatase aptamers to obtain aptamer magnetic nanoparticles;

2) combining the peripheral whole blood sample after removing red blood cells with the aptamer magnetic nanoparticles and then performing magnetic separation to remove non-specific cells to obtain a product containing circulating tumor cells;

3) detecting the product containing circulating tumor cells and determining whether the sample to be tested contains tumor cells expressing or overexpressing alkaline phosphatase based on absorbance or whether a precipitate is formed on the cell surface.

The method for determining whether the sample to be tested contains tumor cells expressing or overexpressing alkaline phosphatase based on absorbance is the following A:

A. the product containing circulating tumor cells is stained with a substrate (such as pNPP) of alkaline phosphatase for color development, and then absorbance is detected; the control aptamer sequence is used as a control, and if the absorbance value is significantly different from that after capture with the control aptamer sequence, the sample to be tested contains or is supposed to contain tumor cells expressing or overexpressing alkaline phosphatase; if the absorbance value is not significantly different from that after capture with the control sequence, the sample to be tested contains no or is supposed to contain no tumor cells expressing or overexpressing alkaline phosphatase;

the method for determining whether the sample to be tested contains tumor cells expressing or overexpressing alkaline phosphatase based on whether a precipitate is formed on the cell surface is the following B:

B. the product containing circulating tumor cells is stained with a substrate (such as BCIP/NBT) of alkaline phosphatase and then observed under a microscope; if cells with a blue-purple precipitate on the surface are observed, the sample to be tested contains or is supposed to contain tumor cells expressing or overexpressing alkaline phosphatase; if there are no cells with blue-purple surfaces, the sample to be tested contains no or is supposed to contain no tumor cells expressing or overexpressing alkaline phosphatase.

The fourth object of the present invention is to provide a method for capturing and/or detecting whether a sample to be tested contains exosomes expressing or overexpressing alkaline phosphatase, comprising the following steps:

1) preparing aptamer magnetic nanoparticles and collecting tumor cell exosomes in the sample to be tested;

the method for preparing aptamer magnetic nanoparticles is connecting magnetic nanoparticles and alkaline phosphatase aptamers to obtain aptamer magnetic nanoparticles;

the method for preparing aptamer magnetic nanoparticles is coupling the streptavidin-modified magnetic nanoparticles and the biotin-labeled alkaline phosphatase aptamers to obtain aptamer magnetic nanoparticles;

the method for collecting tumor cell exosomes in the sample to be tested is collecting tumor cell exosomes from the serum or plasma of the sample to be tested;

2) combining the exosomes with the aptamer magnetic nanoparticles and then performing magnetic separation to remove non-specific cells to obtain a product containing exosomes;

3) detecting the product containing exosomes and determining whether the sample to be tested contains tumor cells expressing or overexpressing alkaline phosphatase based on absorbance of the product containing exosomes or whether a precipitate is formed on the surface of the product.

The method for determining whether the sample to be tested contains tumor cells expressing or overexpressing alkaline phosphatase based on absorbance of the product containing exosomes is the following A:

A. the product containing exosomes is stained with pNPP, and then absorbance is detected; the control aptamer sequence is used as a control, and if the absorbance value is significantly different from that after capture with the control aptamer sequence, the sample to be tested contains or is supposed to contain exosomes expressing or overexpressing alkaline phosphatase; if the absorbance value is not significantly different from that after capture with the control sequence, the sample to be tested contains no or is supposed to contain no exosomes expressing or overexpressing alkaline phosphatase;

the method for determining whether the sample to be tested contains tumor cells expressing or overexpressing alkaline phosphatase based on whether a precipitate is formed on the surface of the product is the following B:

B. the product is stained with BCIP/NBT and then observed under a microscope; if cells with a blue-purple precipitate on the surface are observed, the sample to be tested contains or is supposed to contain exosomes expressing or overexpressing alkaline phosphatase; if there are no cells with a blue-purple precipitate on the surface, the sample to be tested contains no or is supposed to contain no exosomes expressing or overexpressing alkaline phosphatase.

The fifth object of the present invention is to provide a method for capturing and/or detecting whether free proteins in a sample to be tested contain alkaline phosphatase, comprising the following steps:

1) preparing aptamer magnetic nanoparticles and collecting free proteins in the sample to be tested;
the method for preparing aptamer magnetic nanoparticles is connecting magnetic nanoparticles and alkaline phosphatase aptamers to obtain aptamer magnetic nanoparticles;
the method for preparing aptamer magnetic nanoparticles is coupling the streptavidin-modified magnetic nanoparticles and the biotin-labeled alkaline phosphatase aptamers to obtain aptamer magnetic nanoparticles;
the method for collecting free proteins in the sample to be tested is collecting free proteins from the serum or plasma of the sample to be tested;

2) combining the free proteins with the aptamer magnetic nanoparticles and then performing magnetic separation to remove non-specific cells to obtain a product containing free proteins;

3) detecting the product containing free proteins and determining whether the free proteins in the sample to be tested contain alkaline phosphatase based on the absorbance of the product containing free proteins or whether the free proteins can be fluorescently stained.

The method for determining whether the free proteins in the sample to be tested contain alkaline phosphatase based on the absorbance of the product containing free proteins is the following A:

A. the product containing free proteins is stained with pNPP for color development, and then absorbance is detected; the control aptamer sequence is used as a control, and if the absorbance value is significantly different from that after capture with the control aptamer sequence, the free proteins in the sample to be tested contain or are supposed to contain alkaline phosphatase; if the absorbance value is not significantly different from that after capture with the control sequence, the free proteins in the sample to be tested contain no or are supposed to contain no alkaline phosphatase;

the method for determining whether the free proteins in the sample to be tested contain alkaline phosphatase based on whether the free proteins can be fluorescently stained is the following B:

B. the product is developed with fluorescein diphosphate, and then its fluorescence is measured; if fluorescence is observed, the free proteins in the sample to be tested contain or are supposed to contain alkaline phosphatase; if there is no fluorescence or no obvious fluorescence, then the free proteins in the sample to be tested contain no or are supposed to contain no alkaline phosphatase.

The alkaline phosphatase is an alkaline phosphatase heterodimer; and/or the alkaline phosphatase heterodimer is PALP (placental alkaline phosphatase), IAP (intestinal alkaline phosphatase), GCAP (germ cell alkaline phosphatase) or any heterodimer.

DESCRIPTION OF THE DRAWINGS

FIG. 1B showing the binding curve and the apparent binding constant of the aptamer BG2; FIG. 1C showing the binding curve and the apparent binding constant of the aptamer BG2 derivative SEQ ID NO: 2; FIG. 1D showing the binding curve and the apparent binding constant of the aptamer BG2 derivative SEQ ID NO: 3; FIG. 1E showing the binding curve and the apparent binding constant of the aptamer BG2 derivative SEQ ID NO: 4; FIG. 1F showing the binding curve and the apparent binding constant of the aptamer BG2 derivative SEQ ID NO: 5; FIG. 1G showing the binding curve and the apparent binding constant of the aptamer BG2 derivative SEQ ID NO: 6; and FIG. 1H showing the competitive binding assay of BG2 with a variety of sequences.

FIG. 2B showing the flow cytometry assay of alkaline phosphatase heterodimer on the surface of HeLa cells stained by the aptamer BG2; FIG. 2C showing the flow cytometry assay of alkaline phosphatase heterodimer on the surface of MCF-7 cells stained by the aptamer BG2; FIG. 2D showing the flow cytometry assay of alkaline phosphatase heterodimer on the surface of HepG2 cells stained by the aptamer BG2; FIG. 2E showing the flow cytometry assay of alkaline phosphatase heterodimer on the surface of SMMC-7721 cells stained by the aptamer BG2; FIG. 2F showing the flow cytometry assay of alkaline phosphatase heterodimer on the surface of HCT116 cells stained by the aptamer BG2; FIG. 2G showing the flow cytometry assay of alkaline phosphatase heterodimer on the surface of PC-3 cells stained by the aptamer BG2; FIG. 2H showing the flow cytometry assay of alkaline phosphatase heterodimer on the surface of Jurkat cells stained by the aptamer BG2; FIG. 2I showing the flow cytometry assay of alkaline phosphatase heterodimer on the surface of SH-SY5Y cells stained by the aptamer BG2; and FIG. 2J showing the flow cytometry assay of alkaline phosphatase heterodimer on the surface of HEK293 cells stained by the aptamer BG2.

FIG. 7B showing the in vivo imaging of BG2-AF647 in LoVo tumor-bearing mice; and FIG. 7C showing the in vivo imaging of BG2-AF647 in PC-3 tumor-bearing mice.

DETAILED DESCRIPTION OF THE INVENTION

Figure 1:
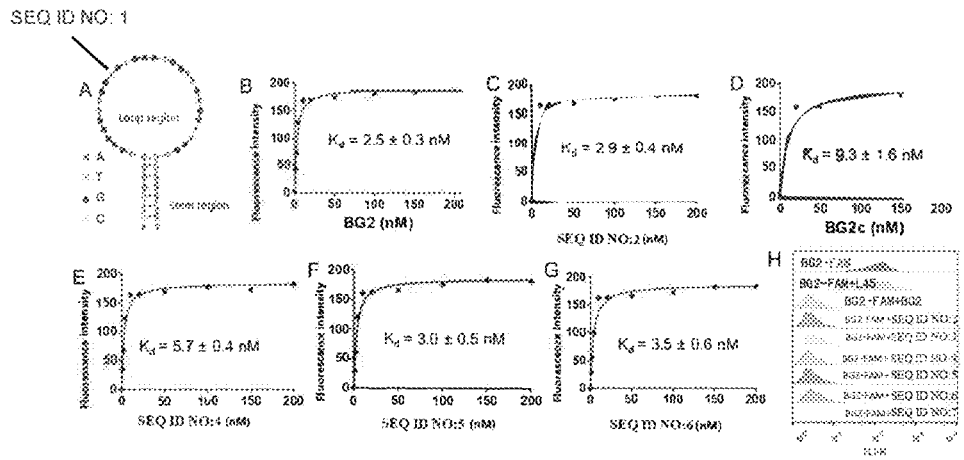
FIG. 1 shows the secondary structure of the aptamer BG2, the apparent binding constants and competition experiments of the aptamer BG2 and its derivatives with FIG. 1A showing the predicted secondary structure of the aptamer BG2.

Unless otherwise specified, the experimental methods used in the following examples are conventional methods.

Unless otherwise specified, the materials and reagents used in the following examples are commercially available.

Binding buffer solution 1:137 mM NaCl, 5 mM $MgCl_2$, 2.7 mM KCl, 2 mM $KH_2PO_4$, 10 mM $Na_2HPO_4$, 25 mM glucose, 1 μg/ml BSA, 0.1 μg/ml herring sperm DNA and 0.01% (v/v) TWEEN®-80, and the rest is water.

Elution buffer (pH=8.0): 137 mM NaCl, 5 mM $MgCl_2$, 2.7 mM KCl, 2 mM $KH_2PO_4$, 10 mM $Na_2HPO_4$, and 25 mM glucose, and the rest is water.

The streptavidin-modified magnetic nanoparticles in the following examples were purchased from Xiamen Purui Maige Biological Technology Co. LTD, and its concentration was 10 mg/mL.

In the following examples, human cervical cancer cells (HeLa), human hepatocellular carcinoma cells (SMMC-7721), human breast cancer cells (MCF-7), human embryonic kidney cells (HEK-293), human neuroblastoma cells (SH-SY5Y) and human leukemia cells (Jurkat E6-1) were purchased from the Institute of Basic Medical Sciences, Chinese Academy of Medical Sciences; human colon cancer cells (LoVo), human hepatocellular carcinoma cells (HepG2), human colon cancer cells (HCT116) and human prostate cancer cells (PC3) were purchased from the Cell Bank of Typical Culture Collection Committee of Chinese Academy of Sciences.

PBS buffer in the following examples: 12 mM $NaH_2PO_4$, 8 mM $Na_2HPO_4$, 122 mM NaCl and 5 mM KCl, and the rest is water.

PBST buffer in the following examples: 12 mM $NaH_2PO_4$, 8 mM $Na_2HPO_4$, 122 mM NaCl, 5 mM KCl and 0.01% (v/v, percentage by volume) Tween-80, and the rest is water.

Binding buffer 2 in the following examples: 12 mM $NaH_2PO_4$, 8 mM $Na_2HPO_4$, 122 mM NaCl, 5 mM KCl, 1 μg/ml bovine serum albumin, 0.1 μg/ml herring sperm DNA and 0.01% (v/v, percentage by volume) Tween-80, and the rest is water.

Working buffer (pH=9.5) in the following examples: 100 mM Tris-HCl, 100 mM NaCl and 5 mM $MgCl_2$.

In the following examples, p-nitrophenyl phosphate disodium salt hexahydrate (pNPP), 5-bromo-4-chloro-3-indolyl phosphate p-toluidine salt (BCIP) and nitro-blue tetrazolium chloride (NBT) were all purchased from J&K SCIENTIFIC® and their catalog numbers are 254303, 338560 and 151804, respectively. Fluorescein diphosphate (FDP) was purchased from THERMO FISHER SCIENTIFIC®, and its catalog number is F2999.

Red blood cell lysis buffer in the following examples was purchased from SIGMA-ALDRICH®, and its catalog number is 11814389001.

Example 1. Screening and Preparation of Aptamers

I. Cell Culture

Human colon cancer LoVo cells, human breast cancer MCF-7 cells, and human cervical cancer HeLa cells were cultured with RPMI 1640 (containing 10% fetal bovine serum, 1% penicillin/streptomycin). All cells were routinely cultured in an incubator (37° C., 5% $CO_2$), and passaged every two to three days.

II. Design of Random Nucleic Acid Library

A random library which was composed of 20 fixed nucleotides at both ends and 45 nucleotides in the middle was designed as follows: 5'-ACGCTCGGATGCCACTA-CAGTYRRRRRRNNGGGNNNGGNNNGGNNGG-NNNN NNNNGGNYYYYYYRTCT-CATGGACGTGCTGGTGAC-3' (SEQ ID NO: 8); N represents A, T, C or G, Y represents T or C, R represents G or A.

III. Selection and Characterization of Aptamer

1. Library Preprocessing 10 nmol random nucleic acid library (synthesized in step II) was dissolved in binding buffer, denatured at 95° C. for 5 min, cooled on ice for 10 min, and placed at room temperature for 30 min for renaturation.

2. Positive Selection $1\times10^6$ human colon cancer LoVo cells, $1\times10^6$ human breast cancer MCF-7 cells and $1\times10^6$ human cervical cancer HeLa cells were respectively digested with PBS containing 5 mM EDTA for 10 min, mixed well, washed once with washing buffer, and the above DNA library was added to the cells for incubation. After incubating for 30 min, the supernatant was removed by centrifugation and the precipitate was washed twice with washing buffer. The DNA molecules bound to the cells were subjected to PCR. The forward primer for the PCR amplification was as follows:

(SEQ ID NO: 9)
5'-FAM-ACGCTCGGATGCCACTACAG-3';

reverse primer:

(SEQ ID NO: 10)
5'-biotin-GTC ACC AGC ACG TCC ATG AG-3'.

PCR amplification procedure: 94° C. for 3 min; 10 cycles of (94° C. for 30 s, 60° C. for 30 s, 72° C. for 30 s); 72° C. for 5 min.

FAM-labeled single-stranded DNA (ssDNA) sequences were isolated from PCR products using streptavidin-modified agarose beads. The obtained ssDNA molecules were desalted with a NAP-5 column (GE MEDICAL SYSTEMS™, Sweden) and dried in vacuum for the next round of selection.

In order to improve the affinity and specificity of aptamers, the number of washings was gradually increased and the number of positive selection cells was gradually decreased during the selection process to increase the selection pressure. After five rounds of selection, high-throughput sequencing was performed.

The aptamer BG2 obtained after removing the primers is as follows:

(SEQ ID NO: 1)
5'-CAAGGAATAGGGGTCGGTGTGGGTGGTTATGATTGGCTTCCTTG-3'.

3. Characterization of Aptamer Affinity

A dish of colon cancer LoVo cells in the logarithmic growth phase was digested with 0.2% EDTA in PBS into a monodisperse cell suspension, and then divided into several aliquots. The aliquots were incubated with a fluorescent molecule-labeled aptamer probe solution for 30 min and washed twice with washing buffer, and then the fluorescence intensity on the cell surface was measured with a BD® FACSCALIBUR™ flow cytometer. The average fluorescence intensity on the cell surface was plotted against the concentration of the aptamer, and the equilibrium dissociation constant $K_d$ of the aptamer was calculated according to the following formula: $Y=B_{max}X(K_d+X)$.

4. Binding of BG2 Aptamer and its Derivatives

The apparent dissociation constant of the BG2 aptamer was determined to be 2.5±0.3 nM (FIG. 1B). In order to study the effect of extended sequence 1 on its binding, the affinity was further determined after the primer sequences were added. The sequence is as follows:

5'-ACGCTCGGATGCCACTACAGtCAAGGAATAGGGGTCGGTGTGGGTGG
TTATGATTGGCTTCCTTGtCTCATGGACGTGCTGGTGAC-3' (SEQ ID
NO: 2, BG2 aptamer derivative).

It was determined that this sequence still maintained a good binding force, and its apparent dissociation constant was 2.9±0.4 nM (FIG. 1C).

As shown in FIG. 1A, after structural analysis of sequence 1, it was found that a loop-stem structure was formed. A series of truncated nucleic acid sequences were designed and synthesized, modified with fluorescent dyes, and then their binding ability to LoVo cells was investigated. The sequence with the strongest binding ability was selected for further applications. The resulting truncated aptamer sequence is as follows:

aptamer BG2c:
GGGGTCGGTGTGGGTGGTTATGATTGG (SEQ ID NO: 3, BG2
aptamer derivative).

As shown in FIG. 1D, when the aptamer was truncated, its affinity decreased to a certain extent (9.3=1.6 nM).

This indicates that GGGGTCGGTGTGGGTGGTTATGATTGG (SEQ ID NO: 3) is the core region for the interaction between the aptamer and the target.

The sequence of the loop region was maintained, and the stem of sequence 1 was subjected to random replacement to obtain new sequences, such as, sequence 4: 5'-TAAGAAATAGGGGTCGGTGTGGGTGGTTATGATTGGCTTTCTTA-3' (SEQ ID NO: 4, BG2 aptamer derivative);

sequence 5:
5'-GATAACATAGGGGTCGGTGTGGGTGGTTATGATTGGCTGTTATC-3'

(SEQ ID NO: 5, BG2 aptamer derivative).

The apparent dissociation constants of sequence 4 and sequence 5 were determined to be 5.7±0.4 nM (FIG. 1E) and 3.0±0.5 nM (FIG. 1F), respectively, indicating that good affinity was still maintained.

In order to improve the stability of the aptamer, the aptamer BG2 was thio-modified, the sequence is as follows:

(SEQ ID NO: 6, BG2 aptamer derivative)
5'-sCsAsAsGsGsAsATAGGGGTCGGTGTGGGTGGTTATGATTGGCsT
sTsCsCsTsTsG-3', wherein sA, sT, sG and sC represent thio-modifications.

It was determined that the thio-modified aptamer still maintained a good affinity, and its apparent dissociation constant was 3.5±0.6 nM (FIG. 1G).

The above results indicate that the BG2 aptamer or its derivatives shown in SEQ ID NOs: 1-6 can bind to colon cancer LoVo cells.

5. Competition Between BG2 Aptamer Derivatives and BG2 Aptamer

The fluorescein-labeled aptamer BG2 (BG2-FAM, 100 nM) was separately mixed with the BG2 aptamer and its derivatives (4 µM) without fluorescent molecules, and about 5×10⁴ LoVo cells were added, respectively, to obtain mixed solutions. The mixed solutions were incubated on ice for 30 min, washed twice with washing buffer, and passed through a 400-mesh sieve, and then detected by a flow cytometer. In addition to the above BG2 derivatives, the following BG2 loop region sequence was also included:

sequence 7:
(SEQ ID NO: 7)
5'-TAGGGGTCGGTGTGGGTGGTTATGATTGGC-3';

the nucleotide sequence of the control nucleic acid sequence L45 is as follows:

(SEQ ID NO: 11)
NNNNNNNNNNNNNNNNNNNNNNNNNNNNNNNNNNNNNNNNNNNNN.

The results are shown in FIG. 1H. Both the unlabeled BG2 aptamer (SEQ ID NO: 1) and its representative derivatives (SEQ ID NOs: 2-7) can competitively bind to the target cells with the fluorescein-labeled BG2 aptamer, indicating that the BG2 derivatives have the same function as the BG2 aptamer.

Example 2. Study on Binding of Aptamer BG2 to Different Types of Cells

I. Preparation of Aptamer BG2 and its Derivatives
1. Synthesis of Aptamer BG2

The aptamer BG2 was synthesized by a DNA synthesizer. The nucleotide sequence of BG2 is as the aptamer follows: 5'-CAAGGAATAGGGGTCGGTGTGGGTGGTTATGATTGGCTTCCTTG-3' (SEQ ID NO: 1). Different molecules can be labeled on the aptamer BG2 according to experimental requirements 2. DNA deprotection: After deprotection with cold ammonia, the synthesized DNA in step 1 was dissolved in TEAA solution;

3. DNA purification: the dissolved DNA in step 2 was purified by PAGE or high performance liquid chromatography;
4. Drying DNA: the purified DNA in step 3 was concentrated by centrifugation and dried;
5. The dried DNA in step 4 was dissolved for later use and its concentration was measured.

II. Preparation of Fluorescein-Labeled Aptamer BG2 Solution (BG2-FAM)

1. Preparation of Fluorescein-Labeled Aptamer BG2-FAM Solution

Fluorescein-labeled aptamer BG2 was obtained by coupling a fluorescein group FAM to the 5' end of the aptamer BG2. BG2-FAM was dissolved in binding buffer and the concentration was calibrated according to UV absorption (200 nM). The resulting mixture was heated at 95° C. for 5 min, placed on ice for 5 min and at room temperature for 15 min to obtain the BG2-FAM solution.

2. Preparation of Fluorescein-Labeled Control Nucleic Acid Solution (L45-FAM) (200 nM)

Fluorescein-labeled control nucleic acid sequence L45 (L45-FAM) was obtained by coupling a fluorescein group FAM to the 5' end of the control nucleic acid sequence L45. The L45-FAM was dissolved in binding buffer and the concentration was calibrated according to UV absorption (100 nM). The resulting mixture was heated at 95° C. for 5 min, placed on ice for 5 min and at room temperature for 15 min to obtain the L45-FAM solution.

The nucleotide sequence of the control nucleic acid sequence L45 is as follows:

```
                                              (SEQ ID NO: 16)
TTTNNNNNNNNNNNNNNNNNNNNNNNNNNNNNNNNNNNNNNNNNNNN.
```

III. Pretreatment of Cell Lines

One dish of each of the following nine cell lines in the logarithmic growth phase: human cervical cancer cells (HeLa), human hepatocellular carcinoma cells (SMMC7721), human breast cancer cells (MCF-7), human embryonic kidney cells (HEK-293), human neuroblastoma cells (SH-SY5Y), human colon cancer cells (HCT116), human prostate cancer cells (PC3) was digested into a monodisperse cell suspension with 5 mM EDTA in PBS, washed twice with washing buffer, divided into several aliquots (the number of cells in each aliquot was $5\times10^4$); the human leukemia cells (Jurkat E6-1) grown in suspension were blown directly by a pipette and washed twice with washing buffer, divided into several aliquots (the number of cells in each aliquot was $5\times10^4$).

IV. Characterization of Expression of Heterodimer in Cell Lines with Antibodies

After the cells were digested with 5 mM EDTA in PBS into a monodisperse cell suspension, they were washed twice with washing buffer. Then the obtained cells were added with 10 μg/mL anti-IAP antibody (Cat. No.: GTX60746, GENETEX®) or 10 μg/mL anti-PALP antibody (Cat. No.: MA1-20245) and incubated for 30 min. After washing once, 4 μg/mL anti-mouse m-IgGκ BP-PE antibody (sc-516141) was added and the resulting mixture was incubated for 30 min. After washing once, the cells were resuspended and detected by a flow cytometer.

V. Detection of Cell Lines by Aptamer BG2

The BG2-FAM solution and the L45-FAM solution prepared in step I of Example 2 were respectively mixed with 10 different cell lines from different sources (the number of cells in each cell line was $5\times10^4$) to obtain mixed solutions. The mixed solutions were incubated on ice for 30 min, washed twice with washing buffer, and passed through a 400-mesh sieve, and then detected by a flow cytometer.

The fluorescence intensity data of the first channel was collected using the FACSCALIBUR® flow cytometer from BD® as the fluorescence intensity on the cell surface. The fluorescence intensity of the aptamer bound on the cell surface in each sample was obtained by subtracting the autofluorescence of the cell from the fluorescence intensity of each sample measured by the instrument.

Use anti-IAP antibody (Cat. No.: GTX60746, GENETEX®) or anti-PALP antibody (Cat. No.: MA1-20245), human colon cancer cells (LoVo), human breast cancer cells (MCF-7), human cervical cancer cells (Hela), human hepatocellular carcinoma cells (SMMC7721) and human hepatocellular carcinoma cells (HepG2) were confirmed to express alkaline phosphatase heterodimers, HCT116 cells underexpressed alkaline phosphatase heterodimers, while PC-3 cells, Jurkat cells, SH-SY5Y cells and HEK293 cells did not express alkaline phosphatase heterodimers.

Figure 2:
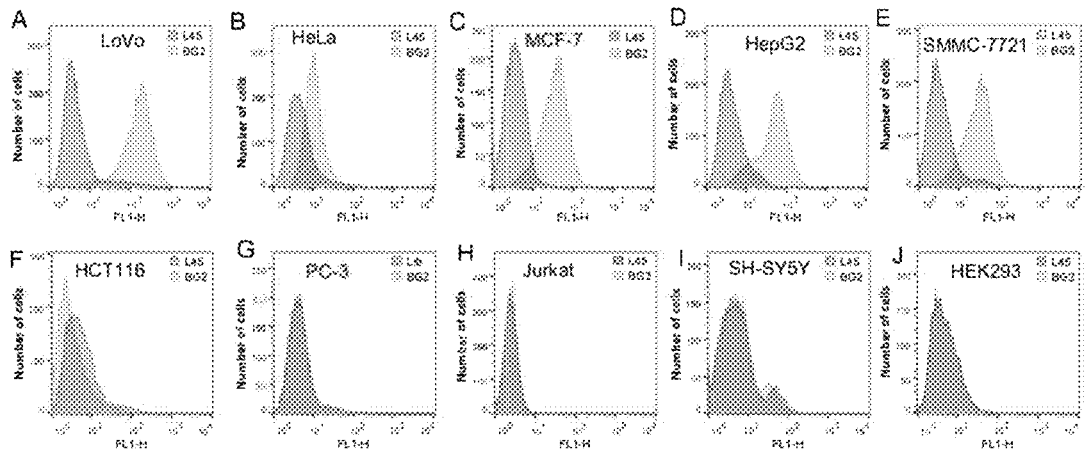
FIG. 2 shows the detection of the expression of alkaline phosphatase heterodimer on the cell surface by aptamers with FIG. 2A showing the flow cytometry assay of alkaline phosphatase heterodimer on the surface of LoVo cells stained by the aptamer BG2.

The results are shown in FIG. 2. It can be seen that the fluorescein-labeled aptamer BG2 bound to human colon cancer cells (LoVo), human breast cancer cells (MCF-7), human cervical cancer cells (Hela), human hepatocellular carcinoma cells (SMMC7721) and human hepatocellular carcinoma cells (HepG2), and weakly bound to HCT116 cells, but not to PC-3 cells, Jurkat cells, SH-SY5Y cells and HEK293 cells.

Example 3. Study on Binding of Aptamer BG2 to Alkaline Phosphatase Heterodimer

I. Synthesis of Aptamer BG2 and its Derivatives

The procedure was the same as step I in Example 2.

II. Preparation of Fluorescein-Labeled Aptamer BG2 Solution (BG2-FAM)

The procedure was the same as step II in Example 2.

III. Knockdown Experiment of Alkaline Phosphatase

1. On the day before transfection, about $3\times10^5$ LoVo cells were seeded in a 6-well plate containing 1640 medium containing 2 mL of FBS and penicillin-streptomycin.
2. When the cells were cultured to 70-90% confluence, the medium was changed to 2 mL of 1640 complete medium without penicillin-streptomycin.
3. In accordance with the relevant instructions of Lipofectamine® RNAiMAX reagent (Cat. No.: 13778-075), 40 pmol of siRNA (siRNA against ALPI was as follows: ALPI-homo-1288, sense sequence (5'-3'): GCAAAGCCUACACGUCCAUTT (SEQ ID NO: 12), antisense sequence (5'-3'): AUGGACGUGUAGGCUUUGCTT (SEQ ID NO: 13); siRNA against PALP: PALP-homo-947, sense sequence (5'-3'): GAGACAUGAAAUACGAGAUTT (SEQ ID NO: 14), antisense sequence (5'-3'): AUCUCGUAUUUCAUGUCUCTT (SEQ ID NO: 15)) was added to 125 μL of serum-free OPTI-MEM® medium and mixed well.
4. 8 μL of LIPOFECTAMINER RNAIMAX® reagent was diluted with 125 μL of serum-free OPTI-MEM® medium and mixed well.
5. The above two diluted alkaline phosphatase siRNA solutions were respectively mixed with LIPOFECTAMINE® RNAIMAX® reagent in a ratio of 1:1 and mixed well. The resulting mixtures were placed at room temperature for 5 min.
6. 250 μL of the mixture of siRNA and LIPOFECTAMINE® RNAIMAX® was added to the wells of a culture plate containing cells and culture medium, and the cell culture plate was shaken back and forth.
7. The cells were cultured in a $CO_2$ incubator at 37° C. for 72 h.
8. After digesting with 5 mM EDTA in PBS into a monodisperse cell suspension, the cells were washed twice with washing buffer. Then the above cells were added with 200 nM BG2-FAM solution. The mixture was incubated on ice for 30 min, washed twice with washing buffer, passed through a 400 mesh sieve, and then detected by a flow cytometer; another portion of the cells was added with 10 μg/mL anti-IAP antibody (Cat. No.: GTX60746, GENETEX®) or 10 μg/mL anti-PALP antibody (Cat. No.: MA1-20245) and incubated for 30 min. After washing once, 4 μg/mL anti-mouse m-IgGκ BP-PE antibody (sc-516141) was added and incubated for 30 min. After washing once, the cells were resuspended and detected by a flow cytometer.

Figure 3:
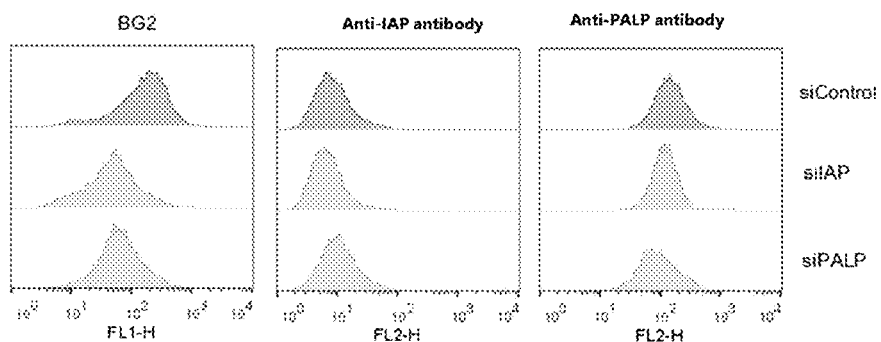
FIG. 3 shows the binding of the aptamer BG2 after knockdown of placental alkaline phosphatase (PALP) or intestinal alkaline phosphatase (IAP).

The results are shown in FIG. 3. After knockdown with siRNA against IAP (siIAP) or siRNA against PALP (siPALP), the binding of aptamer BG2 to the target LoVo cells was reduced.

It is deduced that the aptamer BG2 binds to the IAP protein or the PALP protein of the target LoVo cell.

IV. Overexpression of Alkaline Phosphatase
1. On the day before transfection, about $4\times10^5$ PC-3 cells were seeded in a 6-well plate containing 2 mL of 1640 medium containing FBS and penicillin-streptomycin.
2. When the cells were cultured to 80-90% confluence, the medium was changed to 2 mL of 1640 complete medium without penicillin-streptomycin.
3. In accordance with the relevant instructions of LIPOFECTAMINE® 3000 reagent (Cat. No.: L3000008), 3 μg of IAP, PALP or GCAP plasmid (the IAP (P09923, uniprot database gene ID) or PALP (P05187, uniprot database gene ID) sequence was inserted between the Xho1 and EcoR1 restriction sites of the pCMV-myc vector (YOUBIO™); the GCAP (P10696, uniprot database gene ID) sequence was inserted between the Xho1 and BamH1 restriction sites of the pcDNA3.1(−) vector (YOUBIO™)) was added to 125 μL of serum-free OPTI-MEM® medium, and 5 μL of P3000™ reagent was further added and mixed well.
4. 5 μL of LIPOFECTAMINE® 3000 reagent was diluted with 125 μL of serum-free OPTI-MEM® medium and mixed well.
5. The above diluted plasmid solutions were respectively mixed with Lipofectamine® 3000 reagent in a ratio of 1:1 and mixed well. The resulting mixtures were placed at room temperature for 5 min.
6. 250 μL of the mixture of plasmid and LIPOFECTAMINE® 3000 reagent was added to the wells of a culture plate containing cells and culture medium, and the cell culture plate was shaken back and forth.
7. The cells were cultured in a $CO_2$ incubator at 37° C. for 48 h.
8. After digesting with 5 mM EDTA in PBS into a monodisperse cell suspension, the cells were washed twice with washing buffer. Then the above cells were added with 200 nM BG2-FMA solution. The mixture was incubated on ice for 30 min, washed twice with washing buffer, passed through a 400 mesh sieve, and then detected by a flow cytometer; another portion of the cells was added with 10 μg/mL anti-IAP antibody (Cat. No.: GTX60746, GENETEX®) or 10 μg/mL anti-PALP antibody (Cat. No.: MA1-20245) and incubated for 30 min. After washing once, 4 μg/mL anti-mouse m-IgGκ BP-PE antibody (sc-516141) was added and incubated for 30 min. After washing once, the cells were resuspended and detected by a flow cytometer.

Figure 4:
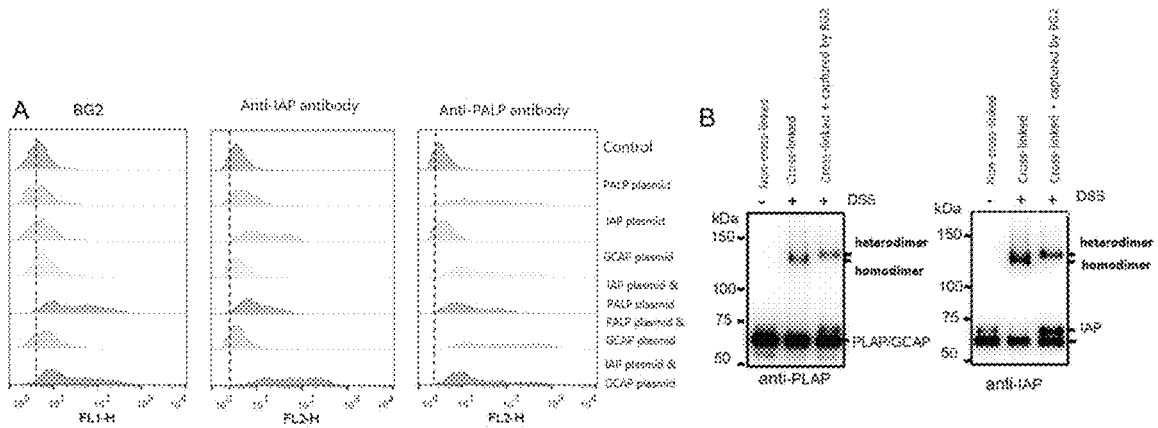
FIG. 4 shows the aptamer BG2 captures alkaline phosphatase heterodimer; with panel A) showing the binding of the aptamer BG2 after placental alkaline phosphatase (PALP), intestinal alkaline phosphatase (IAP), germ cell alkaline phosphatase (GCAP) or heterodimeric protein thereof is expressed and distributed on the surface of PC-3 cells; panel B) shows the capture of alkaline phosphatase heterodimer positive cells by the aptamer BG2.

The results are shown in FIG. 4A. After transfecting the negative cells with PALP plasmid, IAP plasmid or GCAP plasmid, the detections using their antibodies showed that their proteins were expressed on the surface of the cell membrane, but the aptamer BG2 still did not bind to the cells and only when IAP protein and PALP protein or IAP protein and GCAP protein were expressed at the same time, the aptamer BG2 could bind to the cells.

The above results indicate that the aptamer BG2 can bind to IAP/PALP heterodimer or IAP/GCAP heterodimer.

V. In Situ Crosslinking-Capture of Alkaline Phosphatase

Biotin-labeled aptamer BG2 was obtained by coupling a biotin group (bio) containing a disulfide bond to the 5' end of the aptamer BG2. The BG2-SS-bio was dissolved in binding buffer and the concentration was calibrated according to UV absorption (200 nM). The resulting mixture was heated at 95° C. for 5 min, placed on ice for 5 min and at room temperature for 15 min to obtain the BG2-SS-bio solution.

1. $5\times10^6$ LOVO cells in the exponential growth phase were digested with PBS containing 5 mM EDTA, and washed twice with PBS solution.
2. 200 nM BG2-SS-bio solution was added and incubated on ice for 30 min.
3. 25 μL of 100 mM double crosslinking reagent disuccinimidyl suberate (DSS, Thermo Fisher Scientific) was added and incubated on ice.
4. After incubating for 2 h, 25 μL of 1 M Tris-HCl buffer (pH 7.0) was added to stop the crosslinking reaction.
5. The cells were washed twice with PBS and 0.3 mL of cell lysis buffer (sigma) was added to lyse the cells.
6. The precipitate was removed by centrifugation at 2000 rpm and the supernatant was collected. Streptavidin-modified agarose microspheres (GE, Cat. No.: 17-5113-01) were added and incubated for 1 h to extract target proteins.
7. The above extract was added to 4×SDS loading buffer (Bio-Rad) and heated at 60° C. for 10 min.
8. The extract was separated by 6% SDS-PAGE.
9. The proteins were transferred from the gel to a PVDF membrane (Millipore), and then blocked with PBS containing 5% skim milk (SANGON BIOTECH™) and 0.1% Tween-20 for 1 h at room temperature.
10. Anti-IAP antibody (ab186422, ABCAM®) or anti-PALP antibody (ab133602, ABCAM®) was added to the mixture in a ratio of 1:5000, respectively, and incubated at 4° C. overnight.
11. The membrane was washed 5 times with PBST, HRP-labeled secondary antibody at 1:5000 dilution (SANTA CRUZ BIOTECH™) was added, and the membrane was incubated at room temperature for 1 h.
12. The membrane was washed 5 times with PBST, SUPERSIGNAL™ WEST FEMTO™ Maximum Sensitivity Substrate reagent (THERMO FISHER SCIENTIFIC®) was added and the membrane was imaged with a fully automated chemiluminescence image analysis system (such as the TANON™ 5200 from TANON SCIENCE & TECHNOLOGY CO™).

As shown in FIG. 4B, the aptamer BG2 can capture the in-situ crosslinked alkaline phosphatase heterodimer.

The above experiments show that the aptamer BG2 can bind to IAP/PALP heterodimer or IAP/GCAP heterodimer.

Example 4. Study on Binding of Aptamer BG2 to Alkaline Phosphatases of Cells I. Specific Extraction of Alkaline Phosphatases by Aptamer BG2

1. Preparation of Biotin-Labeled Aptamer BG2 and Biotin-Labeled Control Nucleic Acid Sequence L45

(1) Biotin-Labeled BG2 (BG2-Bio)

Biotin-labeled aptamer BG2 (BG2-Bio) was obtained by coupling a biotin group, Bio, to the 5' end of the aptamer BG2. The BG2-Bio was dissolved in binding buffer and the concentration was calibrated according to UV absorption (200 nM). The resulting mixture was heated at 95° C. for 5 min, placed on ice for 5 min and at room temperature for 15 min to obtain the BG2-Bio solution.

(2) Biotin-Labeled Control Nucleic Acid Sequence L45 (L45-Bio)

Biotin-labeled control nucleic acid sequence L45 (L45-Bio) was obtained by coupling a biotin group, Bio, to the 5' end of the control nucleic acid sequence L45. The L45-Bio was dissolved in binding buffer and the concentration was calibrated according to UV absorption (200 nM). The resulting mixture was heated at 95° C. for 5 min, placed on ice for 5 min and at room temperature for 15 min to obtain the L45-Bio solution.

The nucleotide sequence of the control nucleic acid sequence L45 is as follows:

(SEQ ID NO: 16)
TTTNNNNNNNNNNNNNNNNNNNNNNNNNNNNNNNNNNNNNNNNNNNN.

2. Extraction of Alkaline Phosphatases by Aptamer BG2

(1) $2 \times 10^8$ LOVO cells in the exponential growth phase were washed with PBS, and incubated with 200 nM BG2-Bio solution and 200 nM L45-Bio solution (4° C.) for 30 min, respectively, and then formaldehyde was added to fix the cells for 10 min.

(2) The cells were washed twice with PBS, added with 1 mL of cell lysis buffer (R0278-50ML, SIGMA ALDRICH®), and incubated for 1 h.

(3) The mixture was centrifuged at 2000 rpm to remove the precipitate, and the supernatant was collected. Streptavidin-modified agarose microspheres (GE, Cat. No.: GE17-5113-01 from MILLIPORE SIGMA®) were added and incubated for 1 h to extract target proteins. After the incubation, the streptavidin-modified agarose microspheres were obtained.

(4) The streptavidin-modified agarose microspheres obtained after the incubation in step (3) were washed 5 times with PBS to obtain the proteins extracted by the biotin-labeled aptamer BG2 and the proteins extracted by the control nucleic acid sequence L45.

(5) The activity of alkaline phosphatase in the proteins extracted by the biotin-labeled aptamer BG2 and the proteins extracted by the control nucleic acid sequence L45 was determined using alkaline phosphatase detection kit (P0321) from BEYOTIME BIOTECH INC™.

Figure 5:
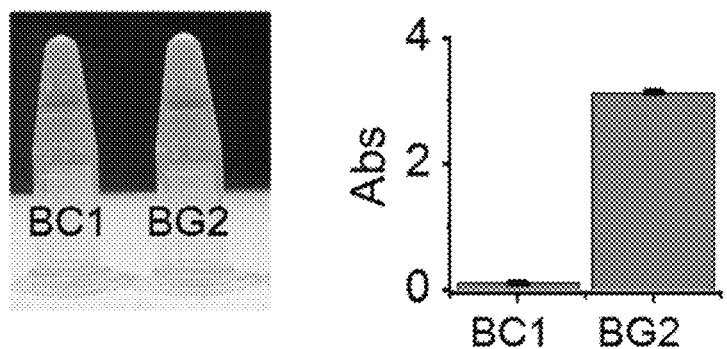
FIG. 5 shows the activity assay of the alkaline phosphatase extracted by the aptamer BG2.

The results are shown in FIG. 5. The left panel is the chromogenic image showing the phosphatase activity of the extracted proteins, and the image in the right panel shows the absorption of the chromogenic solution at 405 nm. It can be seen that the proteins extracted by the biotin-labeled aptamer BG2 can extract the alkaline phosphatases in cellular proteins, which proves that the aptamer BG2 binds to alkaline phosphatases in cells.

II. Extraction of Alkaline Phosphatases and their Interacting Proteins by Aptamer BG2

1. Isotope Labeling of LoVo Cells

Heavy isotope-labeled LoVo cells: heavy isotope-labeled lysine ($[^{13}C_6, ^{15}N_2]$-L-lysine, Cat. No.: 211604102) and heavy isotope-labeled arginine ($[^{13}C_6]$-L-arginine, Cat. No.: 201204102) (SILANTES® GmbH, Germany) were added to RPMI 1640 medium without lysine and arginine to make the concentrations of the heavy isotope-labeled lysine and the heavy isotope-labeled arginine in the medium to be 0.274 mM and 0.575 mM, respectively. LoVo cells were cultured in this medium for 6-7 passages to obtain heavy isotope-labeled LoVo cells for later use.

Light isotope-labeled LoVo cells: light isotope-labeled lysine ($[^{12}C_6, ^{14}N_2]$-L-lysine, Cat. No.: L8662) and light isotope-labeled arginine ($[^{12}C_6]$-L-arginine, Cat. No.: A8094) (SIGMA ALDRICH®) were added to RPMI 1640 medium without lysine and arginine to make the concentrations of the light isotope-labeled lysine and the light isotope-labeled arginine in the medium to be 0.274 mM and 0.575 mM, respectively. LoVo cells were cultured in this medium for 6-7 passages to obtain light isotope-labeled LoVo cells for later use.

2. Preparation of Biotin-Labeled Aptamer BG2 and Biotin-Labeled Control Nucleic Acid Sequence L45

(1) BG2-Bio Solution Labeled with Biotin

Biotin-labeled aptamer BG2 (BG2-Bio) was obtained by coupling a biotin group, Bio, to the 5' end of the aptamer BG2. The BG2-Bio was dissolved in binding buffer and the concentration was calibrated according to UV absorption (200 nM). The resulting mixture was heated at 95° C. for 5 min, placed on ice for 5 min and at room temperature for 15 min to obtain the BG2-Bio solution.

(2) Biotin-Labeled Control Nucleic Acid Sequence L45 (L45-Bio)

Biotin-labeled control nucleic acid sequence L45 (L45-Bio) was obtained by coupling a biotin group, Bio, to the 5' end of the control nucleic acid sequence L45. The L45-Bio was dissolved in binding buffer and the concentration was calibrated according to UV absorption (200 nM). The resulting mixture was heated at 95° C. for 5 min, placed on ice for 5 min and at room temperature for 15 min to obtain the L45-Bio solution.

The nucleotide sequence of the control nucleic acid sequence L45 is as follows:

(SEQ ID NO: 16)
TTTNNNNNNNNNNNNNNNNNNNNNNNNNNNNNNNNNNNNNNNNNNNN.

3. Capture of Proteins Interacting with Alkaline Phosphatases by Aptamer BG2

(1) $2 \times 10^8$ heavy isotope-labeled LoVo cells and light isotope-labeled LoVo cells in the exponential growth phase were washed with PBS, and incubated with 200 nM BG2-Bio solution and L45-Bio solution for 30 min, respectively, and then formaldehyde was added to fix the cells for 10 min.

(2) The cells were washed twice with PBS, added with 1 mL of cell lysis buffer, and incubated for 1 h.

(3) The precipitate was removed by centrifugation at 2000 rpm and the supernatant was collected. Streptavidin-modified agarose microspheres (GB; Cat. No.: GE17-5113-01) were added and incubated for 1 h to extract target proteins.

(4) The streptavidin-modified agarose microspheres obtained after incubation in step (3) were washed 5 times with PBS to obtain heavy isotope-labeled proteins extracted by the biotin-labeled aptamer BG2, light isotope-labeled proteins extracted by the control nucleic acid sequence L45, light isotope-labeled proteins extracted by the biotin-labeled aptamer BG2, and heavy isotope-labeled proteins extracted by the control nucleic acid sequence L45.

4. Forward and Reverse Experiments
   (1) Forward experiment: the heavy isotope-labeled proteins extracted by the biotin-labeled aptamer BG2 and the light isotope-labeled proteins extracted by the control nucleic acid sequence L45 were mixed to obtain a mixed system of the heavy isotope-labeled proteins extracted by the biotin-labeled aptamer BG2 and the light isotope-labeled proteins extracted by the control nucleic acid sequence L45.
   (2) Reverse experiment: the light isotope-labeled proteins extracted by the biotin-labeled aptamer BG2 and the heavy isotope-labeled proteins extracted by the control nucleic acid sequence L45 were mixed to obtain a mixed system of the light isotope-labeled proteins extracted by the biotin-labeled aptamer BG2 and the heavy isotope-labeled proteins extracted by the control nucleic acid sequence L45.

5. Protein Digestion and LC-MS Identification
   (1) DTT reduction: 200 μL of 20 mM dithiothreitol (DTT) was added to the mixed system of the heavy isotope-labeled proteins extracted by the biotin-labeled aptamer BG2 and the light isotope-labeled proteins extracted by the control nucleic acid sequence L45 and the mixed system of the light isotope-labeled proteins extracted by the biotin-labeled aptamer BG2 and the heavy isotope-labeled proteins extracted by the control sequence L45, respectively, and reacted at 56° C. for 45 min.
   (2) IAA alkylation: the product of step (1) was centrifuged and the supernatant was discarded (to remove DTT). 200 μL of 55 mM iodoacetamide (IAA) was added to the precipitate, and reacted at 37° C. in the dark for 30 min.
   (3) The product of step (2) was centrifuged and the supernatant was discarded (to remove IAA). 5 μg of trypsin for mass spectrometry (PROMEGA®, Cat. No.: V5111) was added to the precipitate, and the precipitate was digested overnight at 37° C. to obtain digested polypeptides.
   (4) After the digested peptides were concentrated in vacuo, 100 μL of water was added and desalted using a ZIPTIP® C18 microcolumn. Before mass spectrometry analysis, they were placed in a −20° C. refrigerator.
   (5) The product of step (4) was analyzed and identified by the LTQ-ORBITRAP™ VELOS™ mass spectrometer (THERMO FISHER SCIENTIFIC®, San Jose, CA) to obtain original mass spectrum data.
   (6) Data search and analysis
   Using the MAXQUANT™ search engine (version No.: 1.5.5.1), the original mass spectrum data obtained in step (5) was searched in the uniprot protein database. Some parameters of the database search were as follows: the immobilized modification was the alkylation modification on cysteine, and the variable modification was the oxidation modification on methionine and the acetylation modification on the N-terminus of the protein; two missed cleavages were allowed, the precursor tolerance was 20 ppm, and the mass error of MS/MS fragment ion was 0.5 Da.

The results are shown in Table 1. It can be seen that the aptamer BG2 can bind to the proteins shown in Table 1, including alkaline phosphatases ALPI, ALPP and ALPPL2, as well as proteins that interact with these alkaline phosphatases; this experiment also proved that the aptamer BG2 can be used to detect alkaline phosphatases, such as ALPI, ALPP and ALPPL2.

TABLE 1

Target proteins of aptamer BG2 and their interacting proteins identified by SILAC

| Protein ID | Protein names | Gene names | Unique peptides | Sequence coverage [%] | Score | Ratio (BG2/L45) |
|---|---|---|---|---|---|---|
| P09923 | Intestinal-type alkaline phosphatase | ALPI | 22 | 60 | 323.31 | >20 |
| P05187 | Alkaline phosphatase, placental type | ALPP | 13 | 68.6 | 323.31 | >20 |
| P10696 | Alkaline phosphatase, placental-like | ALPPL2 | 2 | 51.3 | 24.046 | >20 |
| P32004 | Neural cell adhesion molecule L1 | L1CAM | 6 | 5.5 | 53.975 | >20 |
| P01891 | HLA class I histocompatibility antigen, A-68 alpha chain | HLA-A | 1 | 8.3 | 24.706 | >20 |
| P05166 | Propionyl-CoA carboxylase beta chain, mitochondrial | PCCB | 31 | 73.7 | 323.31 | 1.06 ± 0.04 |
| P05165 | Propionyl-CoA carboxylase alpha chain, mitochondrial | PCCA | 40 | 63 | 323.31 | 1.06 ± 0.05 |
| Q96RQ3 | Methylcrotonoyl-CoA carboxylase subunit alpha, mitochondrial | MCCC1 | 35 | 65.9 | 323.31 | 1.02 ± 0.02 |
| P11498 | Pyruvate carboxylase | PC | 70 | 72.3 | 323.31 | 1.00 ± 0.02 |
| Q9HCC0 | Methylcrotonoyl-CoA carboxylase beta chain, mitochondrial | MCCC2 | 30 | 61.6 | 323.31 | 0.94 ± 0.02 |
| B2ZZ90 | Acetyl-CoA carboxylase 1 | ACACA | 41 | 56.3 | 323.31 | 0.94 ± 0.05 |

Example 5. Application of BG2 in Cell Fluorescence Imaging and Tissue Section Fluorescent Staining I. Application of BG2 in Cell Fluorescence Imaging
1. Preparation of Biotin-Labeled Aptamer BG2-Bio Solution (200 nM)
Biotin-labeled aptamer BG2 was obtained by coupling a biotin group, bio, to the 5' end of the aptamer BG2. The BG2-bio was dissolved in binding buffer and the concentration was calibrated according to UV absorption (200 nM). The resulting mixture was heated at 95° C. for 5 min, placed on ice for 5 min and at room temperature for 15 min to obtain the BG2-bio solution.
2. Preparation of Biotin-Labeled Control Sequence Solution (L45-Bio) (200 nM)
Biotin-labeled control sequence L45 (L45-bio) was obtained by coupling a biotin group, bio, to the 5' end of the control sequence L45. The L45-bio was dissolved in binding buffer and the concentration was calibrated according to UV absorption (200 nM). The resulting mixture was heated at 95° C. for 5 min, placed on ice for 5 min and at room temperature for 15 min to obtain the L45-Bio solution. The nucleotide sequence of the control nucleic acid sequence L45 is as follows:

(SEQ ID NO: 16)
TTTNNNNNNNNNNNNNNNNNNNNNNNNNNNNNNNNNNNNNNNNNNNN.

3. Cell Staining
   1) After cultivation on a 35 mm confocal petri dish for one day, LoVo cells (determined to express alkaline phosphatases) were washed once with washing buffer solution, and then incubated with 400 μl of the BG2-bio solution at 37° C. for 30 min. The staining method using the L45-bio solution was the same and the blank was not stained;
   2) The cells were washed twice with washing buffer;
   3) 200 μL of 10 nmol/L streptavidin-modified quantum dots (Q1104/Q1104a, NANOGEN™) was added and incubated for 20 min;
   4) The quantum dots were washed twice with washing buffer;
   3) The quantum dots were observed under a laser scanning confocal microscope or fluorescence microscope.

Figure 6:
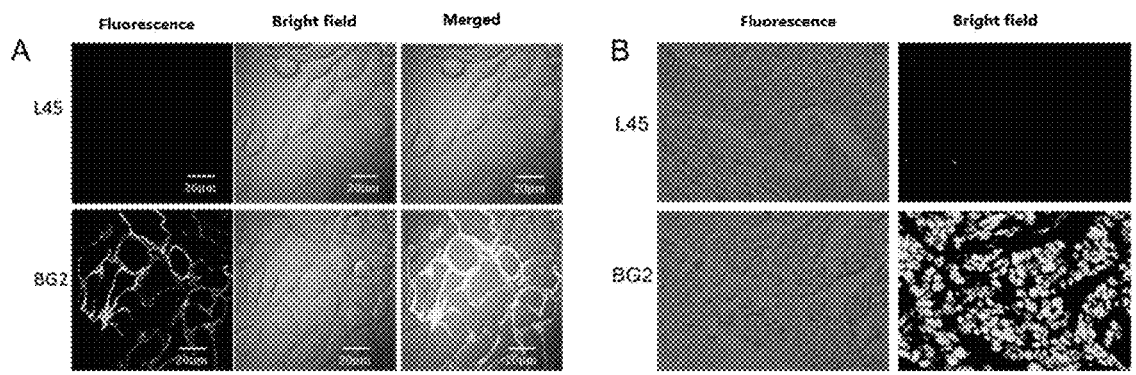
FIG. 6 shows the cell imaging and tissue section immunostaining for detection of phosphatase heterodimer expression by the aptamer BG2; panel A) shows the cell imaging of LoVo cell alkaline phosphatase heterodimer expression realized by the aptamer BG2; panel B) shows the tissue section immunostaining using the BG2 aptamer (top: control sequence L45; bottom: aptamer BG2).

The results are shown in FIG. 6A. It can be seen that BG2 can bind to LoVo cells.

II. Application of BG2 in Tissue Section Fluorescent Staining

A colon cancer tissue section (determined to contain alkaline phosphatases) was stained with the fluorescein-labeled aptamer BG2.

1. Dewaxing and Hydration of Tissue Section
   1) Baking: the section was baked in a 60° C. oven for 60 min;
   2) The section was then immediately placed in a first cylinder of xylene for 15 min, and then placed in a second cylinder of xylene for 15 min;
   3) The section was placed in absolute ethanol for 10 min, 95% ethanol for 5 min, and then 70% ethanol for 5 min;
   4) The section was rinsed with tap water for 5 min (slow-flowing water in a basin) and rinsed once with distilled water.
2. Section Antigen Repair Microwave heat repair method for repairing antigen: an appropriate amount of TE buffer (EDTA 0.292 g, Tris-base 6.05 g, dissolved in 1000 mL of distilled water, pH=8.0) was taken, and the section was placed in a container containing the repairing solution, and placed in a microwave oven to be heated to boiling, and then the heating was stopped to reduce the temperature of the liquid in the container and keep it at 95° C.-98° C. for 15 min. The container was taken out, naturally cooled to room temperature, and the section was taken out, rinsed with distilled water, and then soaked in washing buffer 3 times for 5 minutes each (the washing buffer used in the first soaking should be newly prepared).

3. Incubation and Staining with Aptamer
   1) The section was incubated with binding buffer solution containing 20% FBS and 1 mg/mL herring sperm DNA for 60 min at room temperature;
   2) The section was then incubated with 200 μL of BG2-FAM solution at room temperature for 60 min; the staining method using the control sequence was the same and the blank was not stained;
   3) The section was washed 3 times with washing buffer;
   4) The section was dried and sealed with anti-quench sealant and observed under a laser scanning confocal microscope.

In actual clinical specimen sections, staining can be achieved as shown in FIG. 6B. It can be seen that BG2 can bind to colon cancer tissues.

Example 6. Application of BG2 for In-Vivo Imaging

1. Preparation of Alexa Fluor 647 Fluorescent Molecule-Labeled Aptamer BG2 Solution (BG2-AF647) (3 μM)

ALEXA FLUOR® 647-labeled aptamer BG2 was obtained by coupling an ALEXA FLUOR® 647 group to the 5' end of the aptamer BG2 and conducting thio modifications on the nucleotides 1-7 at the 5' end and the 3' end (SEQ ID NO: 6). The BG2-AF647 was dissolved in binding buffer and the concentration was calibrated according to UV absorption (3 μM). The resulting mixture was heated at 95° C. for 5 min, placed on ice for 5 min and at room temperature for 15 min to obtain the BG2-AF647 solution.

2. Preparation of Alexa Fluor 647 Fluorescent Molecule-Labeled Aptamer BG2 solution (L45-AF647) (3 μM)

ALEXA FLUOR® 647-labeled control sequence L45 was obtained by coupling an ALEXA FLUOR® 647 group to the 5' end of the control sequence L45 and conducting thio modifications on the nucleotides 1-7 at the 5' end and the 3' end. The L45-AF647 was dissolved in binding buffer and the concentration was calibrated according to UV absorption (3 μM). The resulting mixture was heated at 95° C. for 5 min, placed on ice for 5 min and at room temperature for 15 min to obtain the L45-AF647 solution.

The nucleotide sequence of the control sequence L45 is as follows:

(SEQ ID NO: 17)
sNsNsNsNsNsNsNNNNNNNNNNNNNNNNNNNNNNNNNNNNNNNNNsN sNsNsNsNsNsN.

(sN represents thio-modified A, T, G or C, and N is random A, T, G or C)

3. Tumor-Bearing Mouse Model
   1) 4-6 weeks old BALB/c nu/nu male mice were purchased from BEIJING VITAL RIVER LABORATORY ANIMAL TECHNOLOGY CO., LTD.™
   2) 1×10⁷/mL LoVo cells or PC-3 cells (100 μL) in the exponential growth phase were injected subcutaneously into the right armpit with a syringe.
   2) The mice were reared for 3-4 weeks, until the diameter of the tumor reached 0.8-1.2 cm.
   3) 100 μL of the BG2-AF647 solution (3 μM) or the L45-AF647 solution (3 μM) was injected into the mouse vein through the tail vein.
   4) The mice were anesthetized at 30 minutes after injection and were imaged on the MAESTRO™ small animal imaging system (Cambridge Research & Instrumentation). The excitation wavelength was 586-601 nm. The emission light was collected with a 640 nm long-pass filter. The image was processed with MAESTRO™ v2.10.0. After the mice were sacrificed, the tumors were stripped and imaged in the same way.

Figure 7:
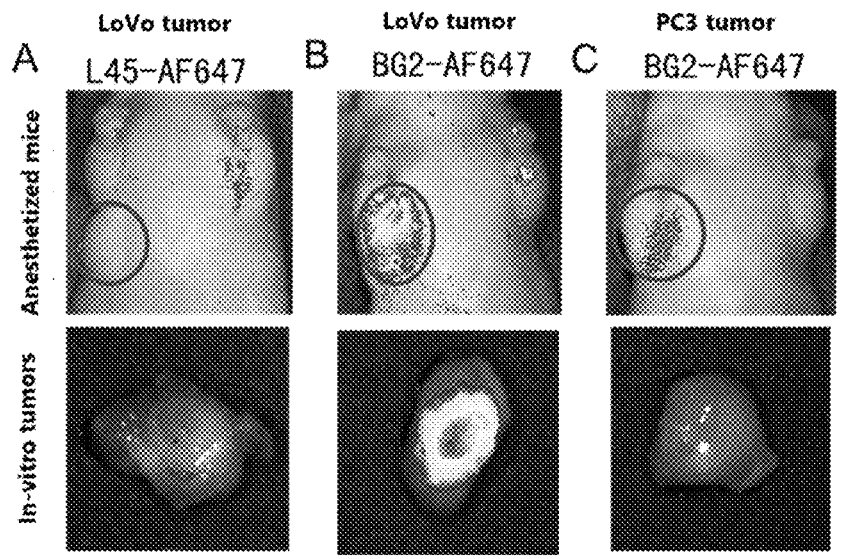
FIG. 7 shows the live animal imaging using the BG2 aptamer (the upper row: live animals; the lower row: isolated tumors) with FIG. 7A showing the in vivo imaging of L45-AF647 in LoVo tumor-bearing mice.

The results are shown in FIG. 7. It can be seen that BG2-AF647 can realize the in vivo imaging of LoVo tumor-bearing mice, and it has good specificity in vivo. BG2-AF647 cannot realize the in vivo imaging of PC-3 tumor-bearing mice.

Example 7. Capture of Tumor Cells by Aptamer BG2

I. Preparation of Magnetic Microspheres and Nanoparticles Coupled with BG2 Aptamers 1. Preparation of Aptamer BG2-Modified Magnetic Microspheres Biotin-labeled aptamer BG2 (BG2-Bio) was obtained by coupling a biotin group, Bio, to the 5' end of the aptamer BG2. The BG2-Bio was dissolved in binding buffer and the concentration was calibrated according to UV absorption (200 nM). The resulting mixture was heated at 95° C. for 5 min, placed on ice for 5 min and at room temperature for 15 min to obtain the BG2-Bio solution.

100 μL of streptavidin-modified magnetic microspheres (Cat. No.: 112.05D, INVITROGEN™ DYNAL™ AS, Norway) solution was added with 1 mL of PBS, shaken, placed on a magnetic stand, and washed twice to obtain magnetic microspheres.

The BG2-Bio solution and the magnetic microspheres were then incubated at room temperature for 30 min, and then washed twice with PBS to obtain BG2-modified magnetic microspheres.

2. Preparation of Control Sequence L45 (L45-Bio)-Modified Magnetic Microspheres

Biotin-labeled control nucleic acid sequence L45 (L45-Bio) was obtained by coupling a biotin group, Bio, to the 5' end of the control sequence L45. The L45-Bio was dissolved in binding buffer and the concentration was calibrated according to UV absorption (200 nM). The resulting mixture was heated at 95° C. for 5 min, placed on ice for 5 min and at room temperature for 15 min to obtain the L45-Bio solution.

The nucleotide sequence of the control nucleic acid sequence L45 is as follows:

(SEQ ID NO: 16)
TTTNNNNNNNNNNNNNNNNNNNNNNNNNNNNNNNNNNNNNNNNNNNNN.

100 μL of streptavidin-modified magnetic microspheres (Cat. No.: 112.05D, INVITROGEN from Dynal AS, Norway) solution was added with 1 mL of PBS, shaken, placed on a magnetic stand, and washed twice to obtain magnetic microspheres.

Then, the L45-Bio solution and the magnetic microspheres were incubated at room temperature for 30 min, and washed twice with PBS to obtain control sequence L45-modified magnetic microspheres.

3. Preparation of Magnetic Nanoparticles Coupled with BG2 Aptamers

10 μL of 10 mg/mL streptavidin-modified magnetic nanoparticles (200 nm) and 10 μL of 1 μM biotin-labeled BG2 aptamer solution (solvent was PBS; solute was BG2-bio) were added to 1 mL of PBST buffer, incubated for 30 min at room temperature with shaking, magnetically separated for 1 min, washed twice with PBST buffer, and magnetically separated to obtain magnetic nanoparticles coupled with BG2 aptamers, i.e., aptamer magnetic nanoparticles.

II. Capture of Cells by Magnetic Microspheres Functionalized by Aptamers

1. Incubation of Cells with Aptamer Magnetic Microspheres:

$1 \times 10^5$ LOVO cells or PC-3 cells in the exponential growth phase were digested with PBS containing 5 mM EDTA, washed twice with PBS solution, and respectively incubated for 30 min with BG2-modified magnetic microspheres and control sequence L45-modified magnetic microspheres at room temperature.

2. Magnetic Separation and Microscope Observation

The mixture was then placed in a magnetic rack and washed 3 times for 3 min each to remove cells that were not bound to the magnetic microspheres. The magnetic ball-cell complexes were resuspended in PBS, dispersed repeatedly, observed under a microscope and photographed.

Figure 8:
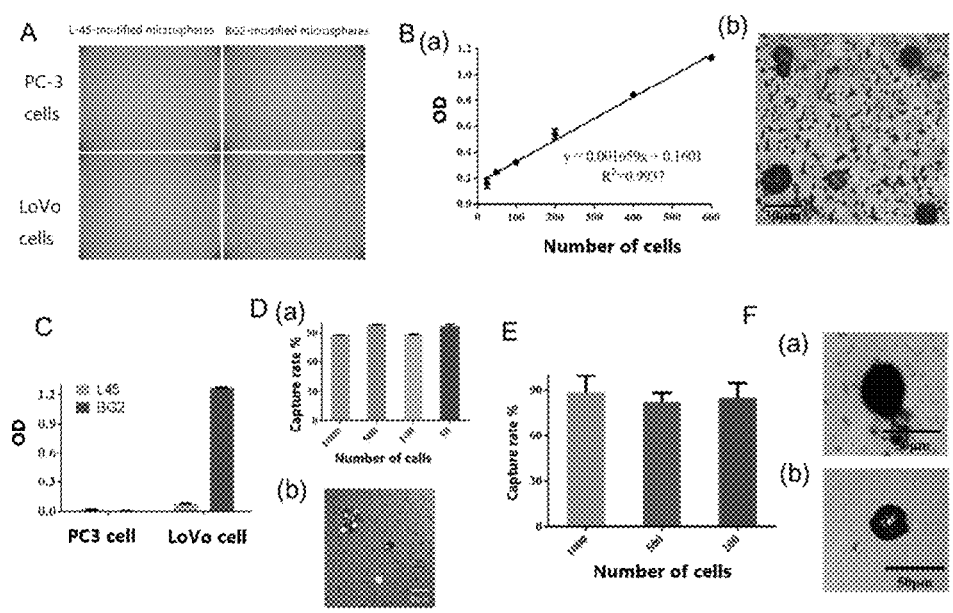
FIG. 8 shows the capture of target cells in the samples to be tested by aptamer microspheres; panel A) shows the capture of cells by aptamer micro-sized magnetic spheres; panel B) shows the results of capture and detection of target cells by aptamer magnetic nanoparticles; panel C) shows the activity of alkaline phosphatase captured by aptamer magnetic particles; panel D) shows the results of capture and detection of target cells by aptamer magnetic nanoparticles in mixed cells; panel E) shows the results of capture and detection of target cells by aptamer magnetic nanoparticles in human whole blood; panel F) shows the results of capture and microscopic examination of target cells by aptamer magnetic nanoparticles in human whole blood.

The results are shown in FIG. 8A. BG2-modified magnetic microspheres can capture LoVo cells expressing alkaline phosphatase heterodimers but cannot capture PC-3 cells negatively expressing alkaline phosphatase heterodimers; while the control sequence-modified magnetic microspheres cannot capture any kind of cells. This shows that the BG2 aptamer can be used for the capture or enrichment of cells with positive expression of alkaline phosphatase heterodimers.

III. Capture and Detection of Target Cells by Aptamer Magnetic Nanoparticles

1. Incubation of Cells with Aptamer Magnetic Nanoparticles:

The cultured LoVo cells were digested with EDTA and then washed twice with PBST buffer. Different numbers of cells (25, 50, 100, 200, 400, 600) were added with 1 mL of binding buffer and then added with 10 μL of the aptamer magnetic nanoparticles in step I, incubated at 4° C. for 30 min with shaking.

2. Magnetic Separation:

The incubated product was placed on a magnetic separation rack for magnetic separation to further remove non-specific cells and washed twice with PBST buffer. After the magnetic separation, the desired tumor cells were obtained.

3. Target Cell Detection:

The tumor cells obtained in step 2 were added with 10 μL of the chromogenic substrate pNPP in working buffer, incubated statically at 37° C. for 2 h, and the absorbance was measured at 405 nm with a microspectrophotometer (NANODROP® 2000). A positive correlation was established according to the absorbance value (OD) and the number of cells, and the results are shown in FIG. 8B (a). It can be seen from FIG. 8B (a) that as the number of cells increased, the absorbance value increased accordingly, showing a positive correlation, which proves the feasibility of the method. The detection limit was 5 cells.

Alternatively, the tumor cells obtained in step I were directly placed under a microscope for observation, and the results are shown in FIG. 8B (b). It can be seen from FIG. 8B (b) that the target LoVo cell surface was wrapped with aptamer magnetic nanoparticles, which proves the effectiveness of the capture method.

IV. Capture and Detection of Target Cells in Mixed Cells by Aptamer Magnetic Nanoparticles 1. Incubation of Cells with Aptamer Magnetic Nanoparticles:

$1 \times 10^5$ LOVO cells or PC-3 cells in the exponential growth phase were digested with PBS containing 5 mM EDTA, washed twice with PBS solution, and incubated at 4° C. for 30 min with BG2-modified magnetic microspheres and control sequence L45-modified magnetic microsphere with shaking, respectively.

The cultured LoVo cells were digested with EDTA and then washed twice with PBST buffer, and different numbers of cells were taken; $1 \times 10^6$ cultured Jurkat cells were centrifuged and washed twice with PBST buffer, added with 1 mL of binding buffer. The LoVo cells were added to the Jurkat cells and then 10 μL of the aptamer magnetic nanoparticles obtained in step I was added and incubated at 4° C. for 30 min with shaking.

2. Magnetic Separation:

The incubated product was placed on a magnetic separation rack for magnetic separation to further remove non-specific cells and washed twice with PBST buffer. After the magnetic separation, the desired tumor cells were obtained.

3. Target Cell Detection:

The tumor cells obtained in the step 2 were added with 10 μL of the chromogenic substrate pNPP in working buffer, incubated statically at 37° C. for 2 h, and the absorbance was measured at 405 nm with a microspectrophotometer. The capture rate was calculated as follows: (capture rate (%)=absorbance value produced by the reaction of cells with a chromogenic substrate after capture/absorbance value produced by the reaction of pure cells (LoVo cells) with a chromogenic substrate×100).

The results are shown in FIG. 8C. The absorbance value of the positive cell sample (LoVo cells) captured by the BG2 aptamer was significantly different from the positive cell sample captured by the control sequence (P<0.01), while the negative samples (PC3 cells) captured by the BG2 aptamer and the control sequence showed no significant difference in absorbance. The results indicate that this method can be used to detect whether the sample to be tested contains tumor cells that express or overexpress alkaline phosphatases.

The results are shown in FIG. 8D (a). 50, 100, 500 and 1000 target LoVo cells were added to $10^6$ non-specific Jurkat cells, and the capture rates were all around 90%.

Alternatively, the tumor cells obtained in step (1) were directly observed under a microscope. The results are shown in FIG. 8D (b). It can be seen that, after the LoVo cells (stained with the dye 4',6-diamidino-2-phenyl indole (blue)) and the PC3 cells (stained with the dye fluorescein diacetic acid (green)) were mixed, the surface of LoVo cells was wrapped with aptamer magnetic nanoparticles, while there were no magnetic nanoparticles on the surface of the non-specific PC3 cells, which proves the specificity of this method.

V. Capture and Detection of Target Cells in Human Whole Blood by Aptamer Magnetic Nanoparticles 1. Incubation of Cells with Aptamer Magnetic Nanoparticles:

The cultured LoVo cells were digested with EDTA and then washed twice with PBST buffer; different numbers of LoVo cells were added to 1 mL of whole blood, and 2 mL of red blood cell lysis buffer was then added. The mixture was gently pipetted to mix, lysed at room temperature for 10 min, centrifuged at 500 g for 5 min. The red supernatant was discarded (if red blood cell lysis is found to be incomplete, repeat the above steps 1-2 times). The cells were washed twice with PBST buffer and the cells were maintained in the precipitate. 1 mL of binding buffer was added to the precipitate, and then 10 μL of the aptamer magnetic nanoparticles obtained in step I was added. The mixture was incubated at 4° C. for 30 min with shaking.

2. Magnetic Separation:

The incubated product was placed on a magnetic separation rack for magnetic separation to further remove non-specific cells and washed twice with PBST buffer. After the magnetic separation, the desired circulating tumor cells were obtained.

3. Target Cell Detection:

The circulating tumor cells obtained in step 2 were added with 10 μL of the chromogenic substrate pNPP in working buffer, incubated statically at 37° C. for 2 h, and the absorbance was measured at 405 nm with a microspectrophotometer. The capture rate was calculated as follows: (capture rate (%)=absorbance value produced by the reaction of cells with a chromogenic substrate after capture/absorbance value produced by the reaction of pure cells (LoVo cells) with a chromogenic substrate×100).

The results are shown in FIG. 8E. When 200, 500, and 1000 target LoVo cells were added to 1 mL of whole blood, the capture rates were all no less than 85%. It proves that this method can also effectively capture and detect cells in human whole blood samples.

VI. Capture of Target Cells in Human Whole Blood by Aptamer Magnetic Nanoparticles and Microscopical Examination of Target Cells BCIP/NBT working solution in the following examples was prepared as follows: BCIP was dissolved in 100% dimethylformamide to a final concentration of 50 mg/mL; NBT was dissolved in 70% dimethylformamide to a final concentration of 50 mg/mL; to each 1 mL of working buffer, 4 μL of NBT was added and mixed well and then 4 μL of BCIP was added and mixed well again. This reagent was prepared and used within 1 h. After reacting with an alkaline phosphatase, a blue-violet precipitate was produced.

1. Incubation of Cells with Aptamer Magnetic Nanoparticles:

The cultured LoVo cells were digested with EDTA and washed twice with PBST buffer; 50 LoVo cells were added to 1 mL of whole blood from a healthy individual, and 2 mL of red blood cell lysis buffer was added. The mixture was gently pipetted to mix, lysed at room temperature for 10 min, centrifuged at 500 g for 5 min. The red supernatant was discarded (if red blood cell lysis is found to be incomplete, repeat the above steps 1-2 times). The cells were washed twice with PBST buffer and 1 mL of binding buffer was added and then 10 μL of the aptamer magnetic nanoparticles was added. The mixture was incubated at 4° C. for 30 min with shaking.

2 mL of red blood cell lysis buffer was added to 1 mL of whole blood from an individual with colon cancer. The mixture was gently pipetted to mix, lysed at room temperature for 10 min, centrifuged at 500 g for 5 min. The red supernatant was discarded (if red blood cell lysis is found to be incomplete, repeat the above steps 1-2 times). The cells were washed twice with PBST buffer and 1 mL of binding buffer was added and then 10 μL of the aptamer magnetic nanoparticles was added. The mixture was incubated at 4° C. for 30 min with shaking.

2. Magnetic Separation:

The incubated product was placed on a magnetic separation rack for magnetic separation to further remove non-specific cells and washed twice with PBST buffer. After the magnetic separation, the desired circulating tumor cells were obtained.

3. Target Cell Detection:

10 μL of BCIP/NBT working solution was added to the tumor cells obtained in step (1). The mixture was incubated at room temperature for 30 min, and directly placed under a microscope for observation.

The results are shown in FIG. 8F. FIG. 8F (a) shows a circulating tumor cell captured in the whole blood plus tumor cells, and FIG. 8F (b) shows a circulating tumor cell captured in the whole blood of the actual cancer patient. It can be seen that, after the reaction of the circulating tumor cells overexpressing alkaline phosphatase with BCIP/NBT, a blue-violet precipitate was produced on the cell surface, which proves that this method is expected to be able to be used for microscopic examination of clinical samples.

Therefore, this efficient, highly selective and rapid capture method is expected to be used in the detection of circulating tumor cells in clinical samples, thereby contributing to the early diagnosis and prognostic evaluation of cancer.

The above results indicate that aptamers and magnetic nanoparticles can be used to detect whether the sample to be tested contains circulating tumor cells. The kit used for the detection includes the following substances:
- a streptavidin-modified magnetic nanoparticle, a biotin-labeled BG2 aptamer, wherein the nucleotide sequence of the BG2 aptamer is as shown in SEQ ID NO: 1 in the sequence listing;
- it further includes other substances used for the capture of circulating tumor cells, such as PBST buffer, binding buffer, red blood cell lysis buffer and a magnetic separation rack;
- it further includes other substances used for the detection of circulating tumor cells, such as a dye capable of binding to alkaline phosphatase (such as chromogenic substrate pNPP or BCIP/NBT), a fluorescent substrate, a spectrophotometer or a microscope.

The specific steps of the detection method were as follows:
1) coupling the streptavidin-modified magnetic nanoparticles and the biotin-labeled BG2 aptamers to obtain aptamer magnetic nanoparticles;
2) combining the sample to be tested with the aptamer magnetic nanoparticles and then performing magnetic separation to remove non-specific cells to obtain a product containing circulating tumor cells;
3) detecting the product containing circulating tumor cells to achieve the capture and/or detection of circulating tumor cells in the sample to be tested.

The method for detecting the product containing circulating tumor cells was the following A or B:
A. the product containing circulating tumor cells was stained with pNPP for color development, and then absorbance was detected; the control aptamer sequence was used as a control; if the absorbance value is significantly different from that after capture with the control aptamer sequence, the sample to be tested contains or is supposed to contain circulating tumor cells; if the absorbance value is not significantly different from that after capture with the control sequence, the sample to be tested contains no or is supposed to contain no circulating tumor cells;
B. the product containing circulating tumor cells was stained with BCIP/NBT and then observed under a microscope; if cells with a blue-purple precipitate on the surface are observed, the sample to be tested contains or is supposed to contain circulating tumor cells; if there are no cells with blue-purple surfaces, the sample to be tested contains no or is supposed to contain no circulating tumor cells.

In the control aptamer L45, the biotin was labeled at the 5' end of L45.

Example 8. Capture and Detection of Exosomes by Aptamer Magnetic Nanoparticles

I. Capture of Exosomes:
(1) Coupling of BG2 Aptamers to Streptavidin-Modified Magnetic Nanoparticles:
1 μL of 10 mg/mL streptavidin-modified 200 nm magnetic nanoparticles and 10 μL of 1 μM biotin-labeled BG2 aptamers were added to 1 mL of PBST buffer. The mixture was incubated at room temperature for 30 min, magnetically separated for 1 min, washed twice with PBST buffer to obtain aptamer magnetic nanoparticles.

(2) Preparation of Exosomes
Exosomes were prepared by the commonly used ultra-high speed centrifugation method. First, LoVo cells were cultured in a medium containing normal serum. After the cell density reached 70-80% confluent, the original medium was replaced with serum-free medium. The cells were further cultured for 48 h. The cell supernatant was collected, centrifuged at 800×g for 10 min at 4° C. The supernatant was pipetted out carefully, centrifuged at 2000×g for 20 min at 4° C. The resulting supernatant was collected, centrifuged at 10000×g for 30 min at 4° C. The supernatant was then collected to ensure the cells or the cell debris were removed completely. The supernatant was centrifuged at 120,000×g for 120 min at 4° C. The supernatant was discarded, and the precipitate was resuspended in PBS buffer, centrifuged at 120000×g for 120 min at 4° C., and the resulting exosomes were dispersed with 200 μL of PBS buffer.

(3) Incubation of Exosomes with Aptamer Magnetic Nanoparticles:
1 mL of binding buffer was added to the exosomes obtained in the step (2) at different concentrations (0.25, 0.5, 1, 2, 4, 8 μg/mL) and then the aptamer magnetic nanoparticles obtained in step (1) were added. The mixture was incubated at 4° C. for 30 min with shaking.

(4) Magnetic Separation:
The incubated product was placed on a magnetic separation rack for magnetic separation and washed twice with PBS buffer. After the magnetic separation, the desired exosomes were obtained.

Figure 9:
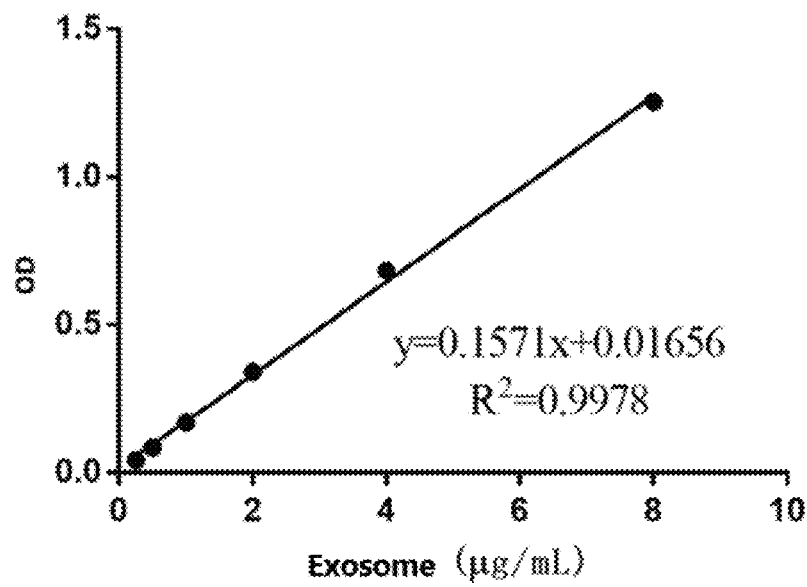
FIG. 9 shows the results of capture and microscopic examination of target cells by aptamer magnetic nanoparticles in exosomes.

II. Exosome Detection:
The exosomes obtained in the step I was added with 10 μL of the chromogenic substrate pNPP in working buffer, incubated statically at 37° C. for 2 h, and the absorbance was measured at 405 nm with a microspectrophotometer (NANODROP® 2000). A positive correlation was established according to the absorbance value and the number of exosomes. The results are shown in FIG. 9. It can be seen from FIG. 9 that as the concentration of exosomes increased, the absorbance value increased accordingly, showing a positive correlation, which proves the feasibility of the method. The detection limit was 0.03 μg/mL.

Example 9. Free Protein Detection of Plasma/Serum Samples from Tumor Patients

I. Capture of Soluble Alkaline Phosphatase:
(1) Coupling of BG2 Aptamers to Streptavidin-Modified Magnetic Nanoparticles:
1 μL of 10 mg/mL streptavidin-modified 200 nm magnetic nanoparticles (conjugated with biotin-labeled oligonucleotide 300 pmol/mg) and 10 μL of 1 μM biotin-labeled BG2 aptamers were added to 1 mL of PBST buffer. The solution was incubated at room temperature with shaking for 30 min, magnetically separated for 1 min, washed twice with PBST buffer to obtain aptamer magnetic nanoparticles.

(2) Incubation of Human Serum/Plasma Samples with Aptamer Magnetic Nanoparticles:
1 mL of binding buffer was added to different amounts of alkaline phosphatase (4, 8, 16, 30, 60, 120 or 240 μU), and then the aptamer magnetic nanoparticles in step (1) were added. The mixture was incubated at 4° C. for 30 min with shaking.

1 mL of binding buffer was added to 10 μL of serum/plasma, and then the aptamer magnetic nanoparticles in step (1) were added. The mixture was incubated at 4° C. for 30 min with shaking.

(4) Magnetic Separation:

The incubated product was placed on a magnetic separation rack for magnetic separation to further remove non-specific cells and washed twice with PBST buffer. After the magnetic separation, the desired soluble alkaline phosphatase in cells were obtained.

Figure 10:
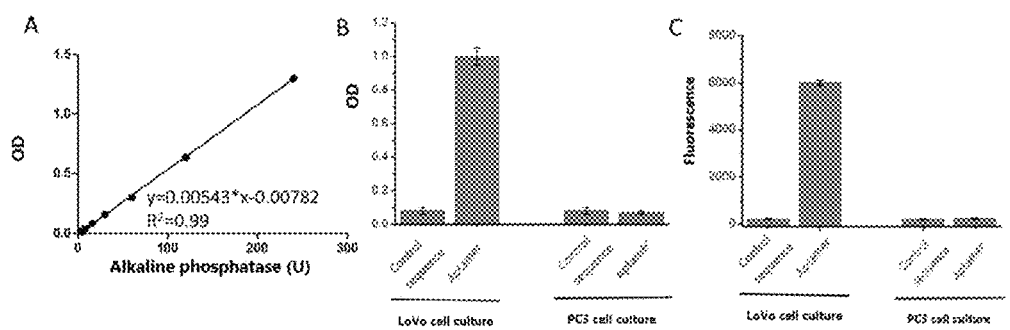
FIG. 10 shows the detection of soluble alkaline phosphatase in the samples to be tested by aptamer magnetic nanoparticles; panel A) shows the results of detection of soluble alkaline phosphatase by aptamer magnetic nanoparticles; panel B) and panel C) shows the results of detection of soluble alkaline phosphatase in cell culture by aptamer microspheres.

II. Detection of Soluble Alkaline Phosphatase:

The soluble alkaline phosphatase obtained in the step I was added with 10 μL of the chromogenic substrate pNPP in working buffer, incubated statically at 37° C. for 2 h, and the absorbance was measured at 405 nm with a microspectrophotometer (NANODROP® 2000). A positive correlation was established according to the absorbance value and the concentration of the soluble alkaline phosphatase. The results are shown in FIG. 10A. It can be seen from FIG. 10A that as the concentration of the soluble alkaline phosphatase increased, the absorbance value increased accordingly, showing a positive correlation, which proves the feasibility of the method.

The measured absorbance value of 10 μL of serum sample was brought into the above standard curve, the concentration of soluble alkaline phosphatase in the serum was calculated to be 20 U/L.

Example 10. Detection of Free Alkaline Phosphatase Heterodimer Protein in Cell Culture (1) 1 mL of LoVo cell culture in the exponential growth phase and 1 mL of PC-3 cell culture in the exponential growth phase were centrifuged at 1000 rpm for 5 min to remove cell debris and incubated for 30 min with 10 nM biotin-labeled BG2 aptamer BG2-Bio solution or biotin-labeled control sequence L45-bio solution (4° C.) with shaking.

(2) 10 μL of streptavidin-modified agarose microspheres (GE, Cat. No.: 17-5113-01) was added and incubated at 4° C. with shaking for 60 min.

(3) The supernatant was removed by centrifugation at 2000 rpm and washed twice with PBST buffer.

(4) The soluble alkaline phosphatase obtained above was added with 10 μL of the chromogenic substrate pNPP in working buffer, incubated statically at 37° C. for 2 h, and the absorbance was measured at 405 nm with a microspectrophotometer (NANODROP® 2000). The results are shown in FIG. 10B.

Alternatively, 100 μL of 10 μM fluorescein diphosphate in working buffer was added to the product obtained in step (3). The mixture was incubated statically at 37° C. for 1 h, and then excited at 488 nm using a microplate reader (SPECTRAMAX® MS) and the emission at 530 nm was measured. The results are shown in FIG. 10C.

As can be seen from FIGS. 10B and 10C, alkaline phosphatase can be captured in the alkaline phosphatase-expressing cell line (LoVo) culture, but not in the negatively expressing cell line (PC3) culture. This proves that this method can be used for the capture and detection of free alkaline phosphatase heterodimer in actual samples.

INDUSTRIAL APPLICATIONS

The present invention finds for the first time that the aptamer BG2 can specifically recognize and bind to alkaline phosphatase heterodimers. The aptamer BG2 of the present invention has the characteristics of high affinity, strong specificity, no immunogenicity and no toxicity, etc. The method for detecting an alkaline phosphatase heterodimer based on the aptamer BG2 can be used for the detection of alkaline phosphatase heterodimer expression and the diagnosis of related diseases. The method for capturing and detecting circulating tumor cells overexpressing alkaline phosphatase in peripheral blood based on aptamer magnetic particle technology of the present invention can achieve highly selective capture and detection of target cells. Magnetic particles can play a role in size enlargement for the enrichment of circulating tumor cells, and also can be used for magnetic separation to achieve high-efficiency capture. By using the enzyme reaction of alkaline phosphatase itself with a chromogenic substrate, the separated circulating tumor cells can be visually detected, thereby realizing signal amplification and improving sensitivity. The capture and detection method of the present invention does not require complicated modification and operation procedures, has simple steps, high efficiency and low cost, and can be used for the detection of clinical samples. The captured tumor cells can be used for further culture or gene testing.

What is claimed is:

1. An aptamer or its derivative, which is any one of the following 1) to 6):
   1) a single-stranded DNA molecule comprising a nucleotide sequence as shown in SEQ ID NO: 1, which binds to alkaline phosphatase or its heterodimers;
   2) a derivative of the aptamer obtained by deletion or addition of one or more nucleotides in the aptamer defined in 1) and having the same function as the aptamer;
   3) a derivative of the aptamer obtained by modifying the backbone of the aptamer defined in 1) into a thiophosphate backbone and having the same function as the aptamer;
   4) a peptide nucleic acid molecule encoded by the aptamer defined in 1) and having the same function as the aptamer; or
   5) a derivative of the aptamer obtained by attaching a signal molecule and/or an active molecule and/or a functional group and/or a radionuclide to one end or the middle of the aptamer defined in any one of 1) to 4) and having the same function as the aptamer; and
   6) a derivative of the aptamer comprising a single-stranded DNA molecule as shown in at least one sequence selected from the group consisting of SEQ ID NO: 2; SEQ ID NO: 3; SEQ ID NO: 4; SEQ ID NO: 5; SEQ ID NO: 6; SEQ ID NO: 7; and mixtures thereof.

2. A method of detecting and extracting alkaline phosphatase comprising:
   using an aptamer or its derivative to perform detection or extraction;
   the target of the detection or extraction is alkaline phosphatase itself, an alkaline phosphatase heterodimer, cells containing alkaline phosphatase or its heterodimers, exosomes containing alkaline phosphatase or its heterodimers, tissue sections containing alkaline phosphatase or its heterodimers, living animals containing alkaline phosphatase or its heterodimers;
   wherein, the aptamer is any one of the following 1) to 6):
   1) a single-stranded DNA molecule having the nucleotide sequence as shown in SEQ ID NO: 1;
   2) a derivative of the aptamer obtained by deletion or addition of one or more nucleotides in the aptamer defined in 1) and having the same function as the aptamer;
   3) a derivative of the aptamer obtained by modifying the backbone of the aptamer defined in 1) into a thiophosphate backbone and having the same function as the aptamer;
   4) a peptide nucleic acid molecule encoded by the aptamer defined in 1) and having the same function as the aptamer; or
   5) a derivative of the aptamer obtained by attaching a signal molecule and/or an active molecule and/or a functional group and/or a radionuclide to one end or the middle of the aptamer defined in any one of 1) to 4) and having the same function as the aptamer;
   6) a derivative of the aptamer comprising a single-stranded DNA molecule as shown in at least one sequence selected from the group consisting of SEQ ID NO: 2; SEQ ID NO: 3; SEQ ID NO: 4; SEQ ID NO: 5; SEQ ID NO: 6; SEQ ID NO: 7; and mixtures thereof;
   wherein, the extraction comprises the following steps:
   1) preparing an aptamer magnetic nanoparticle comprises connecting the aptamer and a magnetic nanoparticle to obtain an aptamer magnetic nanoparticle;
   2) combining a sample to be tested with the aptamer magnetic nanoparticles; and
   3) performing magnetic separation to recover a product containing the aptamer magnetic nanoparticle; and
   the detection comprises the following step:
   detecting the product to determine if the sample to be tested contained the target substance expressing or overexpressing alkaline phosphatase heterodimer based on absorbance or the presence of a precipitate on the aptamer magnetic nanoparticles' surface.

3. The method according to claim 2, wherein a sample for the detection is selected from the group consisting of whole blood, serum, culture, saliva, a tissue section and a living body.

4. The method according to claim 2, wherein the detection method is fluorescence imaging by a microscopic examination.

5. The method according to claim 4, wherein the fluorescence imaging is selected from the group consisting of fluorescence imaging of cells and fluorescence imaging of tissue sections.

6. A kit comprising:
a collection of materials to permit the fixing or coupling an aptamer or its derivative to a carrier;
the collection of materials comprising an aptamer or its derivative; and
a carrier;
- wherein the carrier is selected from the group consisting of a nano-sized particle, a micro-sized particle, or a chip, and
- further wherein the carrier comprises a modified surface to which the aptamer or its derivative can be fixed or coupled;

wherein the aptamer or its derivative is any one of the following 1) to 6):
1) a single-stranded DNA molecule having the nucleotide sequence as shown in SEQ ID NO: 1, which binds to alkaline phosphatase or its heterodimers;
2) a derivative of the aptamer obtained by deletion or addition of one or more nucleotides in the aptamer defined in 1) and having the same function as the aptamer;
3) a derivative of the aptamer obtained by modifying the backbone of the aptamer defined in 1) into a thiophosphate backbone and having the same function as the aptamer;
4) a peptide nucleic acid molecule encoded by the aptamer defined in 1) and having the same function as the aptamer; or
5) a derivative of the aptamer obtained by attaching a signal molecule and/or an active molecule and/or a functional group and/or a radionuclide to one end or the middle of the aptamer defined in any one of 1) to 4) and having the same function as the aptamer;
6) A derivative of the aptamer comprising a single-stranded DNA molecule as shown in at least one sequence selected from the group consisting of SEQ ID NO: 2; SEQ ID NO: 3; SEQ ID NO: 4; SEQ ID NO: 5; SEQ ID NO: 6; SEQ ID NO: 7; and mixtures thereof.

7. The kit according to claim 6, wherein
the carrier is selected from the group consisting of the nano-sized particle, the nanosized particle after modification with a modifier, the micro-sized particle after modification by a modifier, a magnetic nanoparticle, and mixtures thereof;
wherein the modifier is selected from the group consisting of streptavidin, biotin, a carboxyl group, an amino group, and a thiol group.

8. The kit according to claim 6, wherein the kit also includes a chromogenic substrate that reacts with alkaline phosphatase;
and wherein the chromogenic substrate is selected from the group consisting of a fluorescent substrate molecule, a chemiluminescent substrate molecule, and a visible light-emitting substrate molecule.

9. A method for detecting whether a sample to be tested contains a target substance expressing or overexpressing alkaline phosphatase heterodimer, comprising the following steps:
1) preparing aptamer magnetic nanoparticles comprises connecting the aptamers according to claim 6 and magnetic nanoparticles to obtain aptamer magnetic nanoparticles;
2) combining the sample to be tested with the aptamer magnetic nanoparticles; and
3) performing magnetic separation to recover a product containing the aptamer magnetic nanoparticles; and
4) analyzing the product to determine if the sample to be tested contained the target substance expressing or overexpressing alkaline phosphatase heterodimer based on absorbance or the presence of a precipitate on the aptamer magnetic nanoparticles' surface.

* * * * *

SEQUENCE LISTING

<160> NUMBER OF SEQ ID NOS: 17

<210> SEQ ID NO 1
<211> LENGTH: 44
<212> TYPE: DNA
<213> ORGANISM: Artificial Sequence
<220> FEATURE:
<223> OTHER INFORMATION: Synthesized

<400> SEQUENCE: 1
caaggaatag gggtcggtgt gggtggttat gattggcttc cttg       44

<210> SEQ ID NO 2
<211> LENGTH: 86
<212> TYPE: DNA
<213> ORGANISM: Artificial Sequence
<220> FEATURE:
<223> OTHER INFORMATION: Synthesized

<400> SEQUENCE: 2

-continued

```
acgctcggat gccactacag tcaaggaata ggggtcggtg tgggtggtta tgattggctt    60
ccttgtctca tggacgtgct ggtgac                                        86

<210> SEQ ID NO 3
<211> LENGTH: 27
<212> TYPE: DNA
<213> ORGANISM: Artificial Sequence
<220> FEATURE:
<223> OTHER INFORMATION: Synthesized

<400> SEQUENCE: 3 ggggtcgg tgtgggtggt tatgattgg                                       27

<210> SEQ ID NO 4
<211> LENGTH: 44
<212> TYPE: DNA
<213> ORGANISM: Artificial Sequence
<220> FEATURE:
<223> OTHER INFORMATION: Synthesized

<400> SEQUENCE: 4
taagaaatag gggtcggtgt gggtggttat gattggcttt ctta                    44

<210> SEQ ID NO 5
<211> LENGTH: 44
<212> TYPE: DNA
<213> ORGANISM: Artificial Sequence
<220> FEATURE:
<223> OTHER INFORMATION: Synthesized

<400> SEQUENCE: 5
gataacatag gggtcggtgt gggtggttat gattggctgt tatc                    44

<210> SEQ ID NO 6
<211> LENGTH: 44
<212> TYPE: DNA
<213> ORGANISM: Artificial Sequence
<220> FEATURE:
<221> NAME/KEY: misc_feature
<222> LOCATION: (1)..(1)
<223> OTHER INFORMATION: c is thio-modified
<220> FEATURE:
<221> NAME/KEY: misc_feature
<222> LOCATION: (2)..(3)
<223> OTHER INFORMATION: a is thio-modified
<220> FEATURE:
<221> NAME/KEY: misc_feature
<222> LOCATION: (4)..(5)
<223> OTHER INFORMATION: g is thio-modified
<220> FEATURE:
<221> NAME/KEY: misc_feature
<222> LOCATION: (6)..(7)
<223> OTHER INFORMATION: a is thio-modified
<220> FEATURE:
<221> NAME/KEY: misc_feature
<222> LOCATION: (38)..(39)
<223> OTHER INFORMATION: t is thio-modified
<220> FEATURE:
<221> NAME/KEY: misc_feature
<222> LOCATION: (40)..(41)
<223> OTHER INFORMATION: c is thio-modified
<220> FEATURE:
<221> NAME/KEY: misc_feature
<222> LOCATION: (42)..(43)
<223> OTHER INFORMATION: t is thio-modified
<220> FEATURE:
<221> NAME/KEY: misc_feature
<222> LOCATION: (44)..(44)
<223> OTHER INFORMATION: g is thio-modified
<220> FEATURE:
<223> OTHER INFORMATION: Synthesized
```

```
<400> SEQUENCE: 6
caaggaatag gggtcggtgt gggtggttat gattggcttc cttg                    44

<210> SEQ ID NO 7
<211> LENGTH: 30
<212> TYPE: DNA
<213> ORGANISM: Artificial Sequence
<220> FEATURE:
<223> OTHER INFORMATION: Synthesized

<400> SEQUENCE: 7
taggggtcgg tgtgggtggt tatgattggc                                    30

<210> SEQ ID NO 8
<211> LENGTH: 86
<212> TYPE: DNA
<213> ORGANISM: Artificial Sequence
<220> FEATURE:
<221> NAME/KEY: misc_feature
<222> LOCATION: (29)..(30)
<223> OTHER INFORMATION: n is a, c, g, or t
<220> FEATURE:
<221> NAME/KEY: misc_feature
<222> LOCATION: (34)..(36)
<223> OTHER INFORMATION: n is a, c, g, or t
<220> FEATURE:
<221> NAME/KEY: misc_feature
<222> LOCATION: (39)..(41)
<223> OTHER INFORMATION: n is a, c, g, or t
<220> FEATURE:
<221> NAME/KEY: misc_feature
<222> LOCATION: (44)..(45)
<223> OTHER INFORMATION: n is a, c, g, or t
<220> FEATURE:
<221> NAME/KEY: misc_feature
<222> LOCATION: (48)..(55)
<223> OTHER INFORMATION: n is a, c, g, or t
<220> FEATURE:
<221> NAME/KEY: misc_feature
<222> LOCATION: (58)..(58)
<223> OTHER INFORMATION: n is a, c, g, or t
<220> FEATURE:
<223> OTHER INFORMATION: Synthesized

<400> SEQUENCE: 8
acgctcggat gccactacag tyrrrrrrnn gggnnnggnn nggnnggnnn nnnnnggnyy    60
yyyyrtctca tggacgtgct ggtgac                                        86

<210> SEQ ID NO 9
<211> LENGTH: 20
<212> TYPE: DNA
<213> ORGANISM: Artificial Sequence
<220> FEATURE:
<223> OTHER INFORMATION: Synthesized

<400> SEQUENCE: 9
acgctcggat gccactacag                                               20

<210> SEQ ID NO 10
<211> LENGTH: 20
<212> TYPE: DNA
<213> ORGANISM: Artificial Sequence
<220> FEATURE:
<223> OTHER INFORMATION: Synthesized

<400> SEQUENCE: 10
gtcaccagca cgtccatgag                                               20
```

<210> SEQ ID NO 11
<211> LENGTH: 45
<212> TYPE: DNA
<213> ORGANISM: Artificial Sequence
<220> FEATURE:
<221> NAME/KEY: misc_feature
<222> LOCATION: (1)..(45)
<223> OTHER INFORMATION: n is a, c, g, or t
<220> FEATURE:
<223> OTHER INFORMATION: Synthesized

<400> SEQUENCE: 11
nnnnnnnnnn nnnnnnnnnn nnnnnnnnnn nnnnnnnnnn nnnnn            45

<210> SEQ ID NO 12
<211> LENGTH: 21
<212> TYPE: DNA
<213> ORGANISM: Artificial Sequence
<220> FEATURE:
<223> OTHER INFORMATION: Synthesized

<400> SEQUENCE: 12
gcaaagccua cacguccaut t                                        21

<210> SEQ ID NO 13
<211> LENGTH: 21
<212> TYPE: DNA
<213> ORGANISM: Artificial Sequence
<220> FEATURE:
<223> OTHER INFORMATION: Synthesized

<400> SEQUENCE: 13
auggacgugu aggcuuugct t                                        21

<210> SEQ ID NO 14
<211> LENGTH: 21
<212> TYPE: DNA
<213> ORGANISM: Artificial Sequence
<220> FEATURE:
<223> OTHER INFORMATION: Synthesized

<400> SEQUENCE: 14
gagacaugaa auacgagaut t                                        21

<210> SEQ ID NO 15
<211> LENGTH: 21
<212> TYPE: DNA
<213> ORGANISM: Artificial Sequence
<220> FEATURE:
<223> OTHER INFORMATION: Synthesized

<400> SEQUENCE: 15
aucucguauu ucaugucuct t                                        21

<210> SEQ ID NO 16
<211> LENGTH: 48
<212> TYPE: DNA
<213> ORGANISM: Artificial Sequence
<220> FEATURE:
<221> NAME/KEY: misc_feature
<222> LOCATION: (4)..(48)
<223> OTHER INFORMATION: n is a, c, g, or t
<220> FEATURE:
<223> OTHER INFORMATION: Synthesized

<400> SEQUENCE: 16
tttnnnnnnn nnnnnnnnnn nnnnnnnnnn nnnnnnnnnn nnnnnnnn          48

```
<210> SEQ ID NO 17
<211> LENGTH: 47
<212> TYPE: DNA
<213> ORGANISM: Artificial Sequence
<220> FEATURE:
<221> NAME/KEY: misc_feature
<222> LOCATION: (1)..(7)
<223> OTHER INFORMATION: n is thio-modified a, c, g, or t
<220> FEATURE:
<221> NAME/KEY: misc_feature
<222> LOCATION: (8)..(40)
<223> OTHER INFORMATION: n is a, c, g, or t
<220> FEATURE:
<221> NAME/KEY: misc_feature
<222> LOCATION: (41)..(47)
<223> OTHER INFORMATION: n is thio-modified a, c, g, or t
<220> FEATURE:
<223> OTHER INFORMATION: Synthesized

<400> SEQUENCE: 17
nnnnnnnnnn nnnnnnnnnn nnnnnnnnnn nnnnnnnnnn nnnnnnn                    47
```